United States Patent [19]

Rossy et al.

[11] E Patent Number: Re. 33,476

[45] Reissued Date of Patent: Dec. 4, 1990

[54] 6-(ALKANOLAMINOARYL)-3(2H)-PYRIDAZINONE DERIVATIVES, AND THEIR USE

[75] Inventors: Phillip A. Rossy, Hillsdale, N.J.; Marco Thyes, Ludwigshafen, Fed. Rep. of Germany; Albrecht Franke, Wachenheim, Fed. Rep. of Germany; Horst Koenig, Ludwigshafen, Fed. Rep. of Germany; Hans D. Lehmann, Hirschberg, Fed. Rep. of Germany; Josef Gries, Wachenheim, Fed. Rep. of Germany; Ludwig Friedrich, Bruehl, Fed. Rep. of Germany; Dieter Lenke, Ludwigshafen, Fed. Rep. of Germany

[73] Assignee: BASF Akteingesellschaft, Ludwigshafen, Fed. Rep. of Germany

[21] Appl. No.: 189,136

[22] Filed: May 2, 1988

Related U.S. Patent Documents

Reissue of:

[64] Patent No.: 4,636,504
Issued: Jan. 13, 1987
Appl. No.: 571,675
Filed: Jan. 17, 1984

[30] Foreign Application Priority Data

Jan. 22, 1983 [DE] Fed. Rep. of Germany ..... 3302021

[51] Int. Cl.[5] ..... C07D 237/06; A61K 31/50

[52] U.S. Cl. ..... 514/252; 514/253; 514/247; 544/238; 544/235; 544/239

[58] Field of Search ..... 544/235, 238, 239; 514/252, 253

[56] References Cited

U.S. PATENT DOCUMENTS

| | | | |
|---|---|---|---|
| 3,689,652 | 9/1972 | Curran et al. | 424/250 |
| 3,806,509 | 4/1974 | Lebkuecher et al. . | |
| 3,824,271 | 7/1974 | Allen et al. | 260/465 D |
| 3,888,901 | 6/1975 | Allen et al. | 260/465 R |
| 4,271,163 | 6/1981 | Thyes et al. | 424/250 |
| 4,410,529 | 10/1985 | Thyes et al. | 424/250 |
| 4,415,571 | 11/1983 | Thyes et al. | 424/250 |
| 4,873,246 | 8/1989 | Rossy et al. | 544/238 |

FOREIGN PATENT DOCUMENTS

| | | |
|---|---|---|
| 1670158 | 12/1970 | Fed. Rep. of Germany . |
| 2150436 | 4/1972 | Fed. Rep. of Germany . |
| 2123246 | 11/1972 | Fed. Rep. of Germany . |
| 2157453 | 5/1973 | Fed. Rep. of Germany . |
| 2304977 | 8/1974 | Fed. Rep. of Germany . |
| 2727481 | 1/1979 | Fed. Rep. of Germany . |
| 2845475 | 7/1980 | Fed. Rep. of Germany . |
| 2854191 | 7/1980 | Fed. Rep. of Germany . |
| 3022176 | 1/1982 | Fed. Rep. of Germany . |
| 3022177 | 1/1982 | Fed. Rep. of Germany . |
| 3033702 | 4/1982 | Fed. Rep. of Germany . |
| 3209158 | 12/1982 | Fed. Rep. of Germany . |
| 3209159 | 12/1982 | Fed. Rep. of Germany . |
| 53-124279 | 8/1978 | Japan . |
| 1164139 | 9/1969 | United Kingdom . |
| 1386150 | 3/1975 | United Kingdom . |
| 1404022 | 8/1979 | United Kingdom . |

OTHER PUBLICATIONS

Chemical Abstracts, vol. 81, 136169s (1974).

*Primary Examiner*—Nicholas S. Rizzo
*Attorney, Agent, or Firm*—Keil & Weinkauf

[57] ABSTRACT

Novel 6-(acylaminoaryl)-3(2H)-pyridazinones of the formula (I)

where $R^1$, $R^2$, $R^3$, $R^4$, A and B have the meanings given in the description, and their preparation are described-[and inhibiting thrombocyte aggregation and gastric secretion].

The compounds are useful for treating disorders *and inhibiting thrombocyte aggregation and gastric secretion.*

13 Claims, No Drawings

6-(ALKANOLAMINOARYL)-3(2H)-PYRIDAZINONE DERIVATIVES, AND THEIR USE

Matter enclosed in heavy brackets [ ] appears in the original patent but forms no part of this reissue specification; matter printed in italics indicates the additions made by reissue.

The present invention relates to novel 6-(acylaminoaryl)-3(2H)-pyridazinone derivatives, processes for their preparation and their use in the treatment of disorders.

Pharmacologically active 6(acylamino)-4,5-dihydro-3(2H)-pyridazinones have been disclosed, cf. German Laid-Open Applications DOS 1,670,158, DOS 2,123,246, DOS 2,150,436, DOS 2,157,453, DOS 2,304,977, DOS 2,727,481, DOS 2,854,191, DOS 2,845,475, DOS 3,022,176, DOS 3,022,177, DOS 3,033,702, DOS 3,209,158 and DOS 3,209,159, and Japanese Preliminary Published Applications 53/124,279, 58/008,015 and 58/008,016, and the previously unpublished Patents WO 83/01,447 and U.S. Pat. No. 4,397,854. 6-(Acylaminoaryl)-3(2H)-pyridazinones having pharmacological activity have also been disclosed, cf. Japanese Preliminary Published Applications 58/008,015 and 58/008,016, U.S. Pat. No. 4,397,854, and J. Med. Chem. 17 (1974), 273–281.

The substances described in these publications possess antihypertensive, anti-inflammatory, membrane-stabilizing, thrombocyte aggregation-inhibiting, cardiotonic and/or coronary dilator properties, or have a cardiovascular or antiallergic action.

We have found that 6-(acylaminoaryl)-3(2H)-pyridazinone derivatives of the formula I

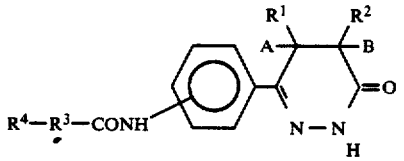

(I)

where the substituents on the phenylene radical are meta or para to one another, A and B are each hydrogen or together form a bond, $R^1$ and $R^2$ are each hydrogen or $C_1$–$C_3$-alkyl, or, where A and B are hydrogen, together form a $C_1$–$C_4$-alkylene radical, $R^3$ is straight-chain $C_1$–$C_4$alkylene which can be substituted by 1 or 2 $C_1$–$C_5$-alkyl groups, and $R^4$ is (a) pyrrol-1-yl, imidazol-1-yl, pyrazol-1-yl or 1,2,4-triazol-1-yl, or (b) a group of the formula II

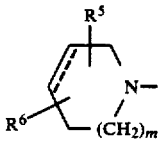

(II)

where the broken line can be an additional bond, $R^5$ and $R^6$ are identical or different and are each hydrogen, a $C_1$–$C_4$-hydrocarbon radical which is unsubstituted or substituted by $C_3$–$C_8$-cycloalkyl or by phenyl which is unsubstituted or substituted by 1 to 3 $C_1$–$C_4$-alkyl, $C_1$–$C_4$-alkoxy, trifluoromethyl and/or nitro groups and/or halogen atoms, or are each $C_3$–$C_8$-cycloalkyl, hydroxyl, trifluoromethyl, $C_1$–$C_4$-acyl, carboxyl, ($C_1$–$C_5$-alkoxy)-carbonyl or cyano, or are each $C_6$–$C_{10}$-aryl which is unsubstituted or mono-substituted, disubstituted or trisubstituted by halogen, $C_1$–$C_4$-alkyl, $C_1$–$C_4$-alkoxy, hydroxyl, trifluoromethyl, $C_1$–$C_4$-acyl, carboxyl, ($C_1$—$C_5$-alkoxy)-carbonyl, cyano, nitro, amino, $C_1$–$C_4$-alkylamino, di-$C_1$–$C_4$-alkylamino, anilino, or $C_1$–$C_4$-acylamino, or are each a 5-membered or 6-membered hetaryl radical which contains 1 to 3 hetero atoms and may or may not be benzofused, or are each a group of the formula $R^7R^8N$—, where $R^7$ and $R^8$ are identical or different and are each hydrogen, $C_1$–$C_8$-alkyl which is unsubstituted or substituted by phenyl which is unsubstituted or substituted by 1 to 3 $C_1$–$C_4$-alkyl, $C_1$–$C_4$-alkoxy, trifluoromethyl and/or nitro groups and/or halogen atoms, or are each phenyl which can be monosubstituted, disubstituted or trisubstituted by halogen, $C_1$–$C_4$-alkyl, $C_1$–$C_4$-alkoxy, trifluoromethyl, $C_1$–$C_4$-acyl, carboxyl, ($C_1$–$C_5$-alkoxy)-carbonyl, cyano and/or nitro, or are each $C_1$–$C_8$-acyl or $C_6$–$C_{10}$-aroyl, and the aroyl group can be monosubstituted, disubstituted or trisubstituted by halogen, $C_1$–$C_4$-alkyl, $C_1$–$C_4$-alkoxy, hydroxyl, trifluoromethyl, $C_1$–$C_4$-alkylthio, $C_1$–$C_4$-alkylsulfoxyl, $C_1$–$C_4$-alkylsulfonyl, $C_1$–$C_4$-acyl, carboxyl, ($C_1$–$C_5$-alkoxy)-carbonyl, cyano, nitro, amino, $C_1$–$C_4$-alkylamino, di-$C_1$–$C_4$-alkylamino or $C_1$–$C_4$-acylamino, or the group $R^7R^8N$— is a benzimidazol-2-on-1-yl radical, or $R^5$ and $R^6$ together form a $C_1$–$C_4$-alkylene chain, the bicyclic structure being unsubstituted or substituted by 1 to 3 $C_1$–$C_3$-alkyl groups, and m is 0, 1, 2 or 3, or (c) a group of the formula III

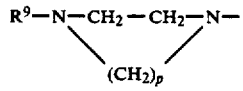

(III)

where $R^9$ is a $C_1$–$C_{14}$-hydrocarbon radical which is unsubstituted or substituted by hydroxyl, $C_3$–$C_8$-cycloalkyl (in which case a $C_5$–$C_8$-cycloalkyl group can be benzofused) or $C_6$–$C_{10}$-aryl which can contain 1 to 3 $C_1$–$C_4$-alkyl, $C_1$–$C_4$-alkoxy, trifluoromethyl, nitro, hydroxyl, $C_1$–$C_4$-acyl, carboxyl, ($C_1$–$C_5$-alkoxy)-carbonyl, amido, N-($C_1$–$C_4$-alkyl)-amido, N,N-di-($C_1$–$C_4$-alkyl)-amido, tri($C_1$–$C_4$-alkyl)-silyl, cyano, amino, $C_1$–$C_4$-alkylamino, di-($C_1$–$C_4$-alkyl)-amino, $C_1$–$C_4$-acylamino groups and/or halogen atoms; a $C_6$–$C_{10}$-aroyl group which is unsubstituted or substituted by 1 to 3 $C_1$–$C_4$-alkyl, $C_1$–$C_4$-alkoxy, trifluoromethyl, nitro, hydroxyl, $C_1$–$C_4$-acyl, carboxyl, $C_1$–$C_5$-alkoxycarbonyl, N,N-di-($C_1$–$C_4$-alkyl)-amido, cyano, di-($C_1$–$C_4$-alkyl)-amino groups and/or halogen atoms; or a hetaroyl group having 5 or 6 ring members, which can contain 1 to 3 hetero atoms and may be benzofused; a $C_3$–$C_{12}$-cycloalkyl, $C_1$–$C_8$-acyl or ($C_1$–$C_5$-alkoxy)-carbonyl group or a $C_6$–$C_{10}$-aryl radical which is unsubstituted or monosubstituted, disubstituted or trisubstituted by halogen, $C_1$–$C_4$-alkyl, $C_1$–$C_4$-alkoxy, hydroxyl, trifluoromethyl, $C_1$–$C_4$-acyl, carboxyl, ($C_1$–$C_5$-alkoxy)-carbonyl, cyano, nitro, amino, $C_1$–$C_4$-alkylamino, di-$C_1$–$C_4$-alkylamino, arylamino or $C_1$–$C_4$-acylamino; or a 5-membered or 6-membered hetaryl radical which may be benzofused, contains 1 to 3 nitrogen atoms and may or may not contain an oxygen atom or a sulfur atom, and p is 2 or 3, or (d) a group of the formula IV $$-NR^{10}R^{11} \quad (IV)$$

where $R^{10}$ and $R^{11}$ are each hydrogen or a $C_1$–$C_{12}$-hydrocarbon radical which is unsubstituted or substituted by one or two phenyl radicals, which may possess 1 to 3 $C_1$–$C_4$-alkyl, $C_1$–$C_4$-alkoxy, trifluoromethyl and/or nitro groups and/or halogen atoms, or by naphthyl, $C_3$–$C_8$-cycloalkyl which can contain 1 to 3 $C_1$–$C_4$-alkyl groups (in which case $C_5$–$C_8$-cycloalkyl groups can be benzofused), or a $C_7$–$C_{10}$-bicycloalkyl group which can contain 1 to 3 $C_1$–$C_4$-alkyl groups;

$C_3$–$C_{12}$-cycloalkyl which can be substituted by 1 to 3 $C_1$–$C_4$-hydrocarbon radicals which can contain a phenyl group (which can be monosubstituted, disubstituted or trisubstituted by $C_1$–$C_4$-alkyl, $C_1$–$C_4$-alkoxy, trifluoromethyl, nitrile, nitro and/or halogen) or a $C_3$–$C_6$-cycloalkyl group, or by a phenyl group (which can contain 1 to 3 $C_1$–$C_4$-alkyl, $C_1$–$C_4$-alkoxy, trifluoromethyl, nitrile or nitro groups and/or halogen atoms) or a $C_3$–$C_8$-cycloalkyl group; a bicyclic or tricyclic $C_7$–$C_{10}$-alkyl radical which can be substituted by 1 to 3 $C_1$–$C_4$-alkyl groups, or a benzofused $C_5$–$C_7$-cycloalkyl group, or (e) a group of the formula V

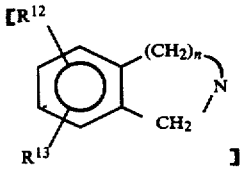

(V)

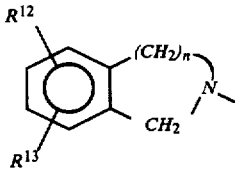

where $R^{12}$ and $R^{13}$ are each hydrogen, halogen, $C_1$–$C_4$-alkyl or $C_1$–$C_4$-alkoxy, and n is 1, 2 or 3, or (f) a group of the formula VI

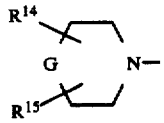

(VI)

where G is oxygen or sulfur, and $R^{14}$ and $R^{15}$ are each hydrogen or $C_1$–$C_4$-alkyl, with the proviso that if $R^1$, $R^2$, A and B are each hydrogen, and the acylamino group is in the para position on the phenyl ring in I, $R^3$ must not be an unsubstituted or $C_1$–$C_5$-alkyl-substituted methylene group, and if $R^2$, A and B are each hydrogen, $R^1$ is hydrogen or $C_1$–$C_3$-alkyl and $R^3$ is unsubstituted or $C_1$–$C_4$-alkyl-substituted methylene, then $R^4$ must not be a group of the formula V where $R^{10}$ and $R^{11}$ are each hydrogen or unsubstituted $C_1$–$C_4$-alkyl, and their salts with physiologically tolerated acids have useful pharmacological properties.

The substituents on the phenyl ring are preferably in the para position.

Preferably, $R^1$ and $R^2$ are hydrogen or methyl, or together form a $C_1$- or $C_2$-alkylene radical. $R^1$ is particularly preferably hydrogen or, where A and B are each hydrogen, methyl. $R^2$ is particularly preferably hydrogen or, where A and B together constitute a bond, methyl.

If $R_1$ and $R_2$ together form a $C_1$–$C_4$-alkylene group, this is very particularly preferably methylene.

Preferably, A and B are each hydrogen or together constitute a bond, but they are particularly preferably hydrogen.

$R^3$ is preferably a straight-chain $C_1$–$C_4$-alkylene group which can be substituted by a $C_1$–$C_3$-alkyl or by two methyl groups. $R^3$ is particularly preferably a $C_1$–$C_3$-alkylene group, in particular methylene or ethylene, which can be substituted by methyl.

Among the radicals $R^4$ stated under (a), the 1-imidazol-1-yl radical is preferred.

If $R^4$ is a group of the formula II, $R^5$ is preferably hydrogen or $C_1$–$C_4$-alkyl which is unsubstituted or substituted by phenyl, or $C_3$–$C_6$-cycloalkyl, or phenyl which can be unsubstituted or substituted by 1 or 2 halogen atoms, $C_1$–$C_4$-alkyl groups, $C_1$–$C_4$-alkoxy groups and/or a trifluoromethyl, nitrile and/or nitro group, or is preferably a group of the formula $R^7R^8N$—, where $R^7$ is hydrogen or phenyl which can be monosubstituted or disubstituted by halogen atoms, $C_1$–$C_4$-alkyl groups, $C_1$–$C_4$-alkoxy groups and/or a nitrile and/or nitro group, and $R^8$ is $C_1$–$C_4$-acyl or benzoyl, or $R^7$ and $R^8$, together with the nitrogen atom, form a benzimidazol-2-on-1-yl group.

$R^6$ is preferably hydrogen, $C_1$–$C_4$-alkyl, hydroxyl, $C_1$–$C_4$-acyl, ($C_1$–$C_5$-alkoxy)-carbonyl or cyano.

$R^5$ is particularly preferably phenyl-substituted $C_1$–$C_4$-alkyl, unsubstituted or halogen-substituted phenykl, or a group of the formula $R^7R^8N$, where $R^7$ is phenyl and $R^8$ is $C_1$–$C_4$-acyl. Among these radicals, benzyl and unsubstituted or halogen-substituted phenyl are particularly noteworthy.

If $R^5$ and $R^6$ together form a $C_1$–$C_4$-alkylene chain, chains which are unsubstituted or substituted by 1 to 3 methyl groups are preferred.

m is preferably 0, 1 or 2, particularly preferably 1.

If $R^4$ is a group of the formula III, $R^9$ is preferably one of the following radicals: a $C_1$–$C_3$-hydrocarbon radical which can be substituted by naphthyl or by phenyl which is unsubstituted or monosubstituted or disubstituted by halogen, $C_1$–$C_4$-alkyl or $C_1$–$C_4$-alkoxy and/or a trifluoromethyl, hydroxyl, $C_1$–$C_4$-acyl, ($C_1$–$C_5$-alkoxy)-carbonyl, nitro and/or nitrile group; naphthyl; phenyl which may be monosubstituted, disubstituted or trisubstituted by halogen, $C_1$–$C_4$-alkyl or $C_1$–$C_4$-alkoxy and/or by a trifluoromethyl or $C_1$–$C_4$-acyl group; or a 6-membered hetaryl radical containing 1 or 2 nitrogen atoms.

$R^6$ is particularly preferably a $C_1$–$C_3$-hydrocarbon radical which is substituted by phenyl which is unsubstituted or $C_1$–$C_4$-alkoxy-substituted; naphthyl; phenyl which can be substituted by 1 or 2 halogen atoms, $C_1$–$C_4$-alkyl groups or $C_1$–$C_4$-alkoxy groups and/or a trifluoromethyl group; or pyridyl. Benzyl which can be substituted by methoxy, phenyl which can be substituted by halogen, and pyridyl are particularly important.

p is preferably 2.

If $R^4$ is a group of the formula IV, $R^{10}$ preferably has one of the following meanings:

$C_1$–$C_8$-alkyl which is unsubstituted or substituted by phenyl which can contain 1 or 2 $C_1$–$C_4$-alkyl groups and/or halogen atoms; $C_3$–$C_{12}$-cycloalkyl which can be substituted by 1 to 3 methyl groups, a benzyl radical or a phenyl radical; a bicyclic or tricyclic $C_7$–$C_{10}$-alkyl radical which is unsubstituted or substituted by 1 to 3 methyl radicals, or a benzofused $C_5$–$C_7$-cycloalkyl group.

$R^{10}$ particularly preferably has one of the following meanings: $C_1$–$C_4$-alkyl which is substituted by phenyl; $C_6$–$C_8$-cycloalkyl which can be substituted by phenyl; or a benzofused $C_5$–$C_6$-cycloalkyl group.

$R^{11}$ is preferably hydrogen or $C_1$–$C_8$-alkyl, in particular hydrogen or $C_1$–$C_4$-alkyl.

If $R^4$ is a group of the formula V, $R^{12}$ and $R^{13}$ are each preferably hydrogen, halogen or $C_1$–$C_4$-alkyl, and n is 1 or 2. $R^{12}$ and $R^{13}$ are each particularly preferably hydrogen, and n is particularly preferably 2.

If $R^4$ is a group of the formula VI, G is preferably oxygen or sulfur, and $R^{14}$ and $R^{15}$ are each preferably hydrogen or methyl.

$R^4$ is preferably a group of the formula II, III, IV or V, particularly preferably a group of the formula II, III or V.

The compounds of the formula I in which A, B and $R^2$ are each hydrogen are 6-aryl-4,5-dihydro-3(2H)-pyridazinones, while compounds of the formula I in which A and B are each hydrogen and $R^1$ and $R^2$ together form a methylene, ethylene, propylene or butylene group are 2-aryl-3,4-diazabicyclo[4.1.0]hept-2-en-5-ones, 2-aryl-3,4-diazabicyclo[4.2.0]oct-2-en-5-ones, 2-aryl-3,4-diazabicyclo[4.3.0]non-2-en-5-ones or 2-aryl-3,4-diazabicyclo[4.4.0]dec-2-en-5-ones.

Compounds of the formula I which A and B together constitute a bond are 6-aryl-3(2H)-pyridazinones.

Examples of suitable physiologically tolerated acids are hydrochloric acid, sulfuric acid, phosphoric acid, acetic acid, citric acid, tartaric acid, malonic acid, succinic acid, maleic acid, fumaric acid, malic acid, lactic acid, diamidosulfonic acid, glutamic acid and aspartic acid.

The novel compounds of the formula I and their salts with physiologically tolerated acids can be prepared by a method in which (a) a compound of the formula VII

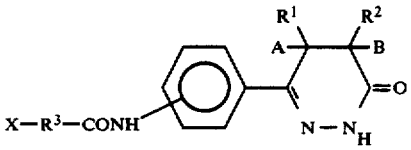

(VII)

where the substituents on the phenylene radical are para or meta to one another, X is halogen and A, B, $R^1$, $R^2$ and $R^3$ have the stated meanings, is reacted with a compound of the formula VIII $$R^4—H \quad (VIII)$$

where $R^4$ has the stated meanings, or (b) an aminophenylpyridazinone of the formula IX

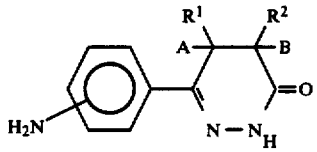

(IX)

where the $NH_2$ group is in the para or meta position, and A, B, $R^1$ and $R^2$ have the stated meanings, is acylated with a compound of the formula X $$R^4—R^3—CO—Y.HY \quad (X)$$

where $R^3$ and $R^4$ have the stated meanings and Y is chlorine or bromine, or (c) a ketocarboxylic acid of the formula XI

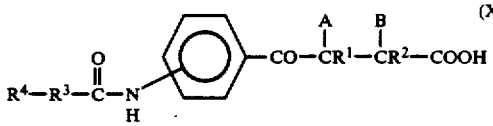

(XI)

where A, B, $R^1$, $R^2$, $R^3$ and $R^4$ have the stated meanings, and the acylamino group is in the para or meta position, is cyclized with hydrazine, or (d) where A and B together constitute a bond and $R^2$ is methyl, a dihydropyridazinone of the formula I

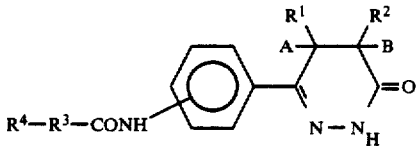

(I)

where $R^1$, $R^3$ and $R^4$ have the stated meanings, and A, B and $R^2$ are each hydrogen, is reacted with formaldehyde, and the resulting compound is, if desired, converted to its salts with physiologically tolerated acids.

Reaction (a) is carried out under conventional conditions, ie. as a rule using not less than an equimolar amount of the compound of the formula VIII in the presence of not less than an equimolar amount of a base as an acid acceptor, with or without the addition of an iodide as a catalyst if X is not iodine, advantageously in the presence of a solvent, at from 0° to 140° C., preferably from 30° to 100° C., if appropriate at the boiling point of the reaction mixture, and under atmospheric or superatmospheric pressure. It is also possible to dispense with the addition of a base, in which case it is advantageously to use not less than two equivalents of the compound of the formula VIII.

Suitable solvents are those which are inert under the reaction conditions, such as aromatic hydrocarbons, eg. toluene or xylene, aliphatic or aromatic hydrocarbons, eg. methylene chloride, ethylene chloride or chlorobenzene, cyclic aliphatic ethers, eg. tetrahydrofuran or dioxane, lower alkanols, eg. methanol, ethanol or isopropanol, aliphatic ketones, eg. acetone, diethyl ketone or methyl ethyl ketone, or dialkylamides, eg. dimethylformamide or N-methylpyrrolidone. Bases used as acid acceptors are advantageously inorganic bases, eg. sodium carbonate, potassium carbonate, sodium bicarbonate or potassium bicarbonate, tertiary organic amines, eg. triethylamine, or an excess of the amine $R^4H$.

Iodides used as catalysts are advantageously alkali metal iodides, preferably potassium iodide or sodium iodide, or quaternary ammonium iodides, eg. tetrabutylammonium iodide. The iodide is used as a rule in an amount of from 1 to 10 mole %. However, it is also possible to employ as much as a molar amount of the catalyst.

The substances of the formula VII which are used as starting compounds are known, or can be prepared by a conventional method.

Reaction (b) takes place under conditions conventionally used for N-acylation, as a rule using not less than an equimolar amount of the acid halide, advantageously in the presence of a solvent, in the presence or absence of an acid acceptor, at from 0° to 100° C., preferably at no higher than 70° C., if appropriate at the boiling point of the reaction mixture, and under atmospheric or superatmospheric pressure.

Solvents preferably used on an industrial scale are ketones, eg. acetone, diethyl ketone or methyl ethyl ketone; otherwise, preferred solvents are, for example, aromatic hydrocarbons, such as benzene, toluene or xylene, cyclic ethers, such as tetrahydrofuran or dioxane, aliphatic or aromatic chlorohydrocarbons, such as methylene chloride, ethylene chloride or chlorobenzene, or dialkylamides, such as dimethylformamide or N-methylpyrrolidone. Acid acceptors are advantageously weak inorganic bases, eg. sodium carbonate, potassium carbonate, sodium bicarbonate or potassium bicarbonate, or organic bases, eg. tertiary amines.

The substances of the formula IX which are used as starting compounds are known, or can be prepared by a conventional method.

The cyclization reaction (c) with hydrazine, which is preferably used in the form of the hydrate, is advantageously carried out in a solvent, in particular a lower alcohol, such as methanol, ethanol or propanol, a cyclic aliphatic ether, such as tetrahydrofuran or dioxane, or a dialkylamide, in particular dimethylformamide or N-methylpyrrolidone, at from 20° to 150° C., preferably from 50° to 100° C. In this reaction, as a rule, 1 mole of hydrazine or hydrazine hydrate is used per mole of XI.

Reaction (d) is advantageously carried out in a solvent, such as a lower alkanol, eg. methanol, ethanol is isopropanol, or a dialkylamide, eg. dimethylformamide or N-methylpyrrolidone, in the presence of a base, eg. NaOH, KOH or $K_2CO_3$, or of a tertiary amine, at from 20° to 150° C., preferably from 50° to 100° C. Advantageously, from 1 to 1.5 moles of formaldehyde are used per mole of I (where A, B and $R^2$ are each H). The reaction can be carried out under atmospheric or superatmospheric pressure.

The compound of the formula XI which are used as starting materials can be prepared by acylating an aminoacid of the formula XII

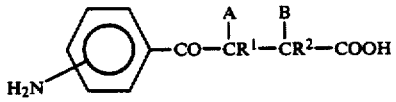

(XII)

where A, B, $R^1$ and $R^2$ have the meanings given for formula I, with a compound of the formula X under the conditions stated for the acylation of a compound of the formula IX with a compound of the formula X, and, where the resulting compound is the hydrochloride or the hydrobromide of a compound of the formula XI, converting this product to the free amino acid.

The compounds of the formula XII are known, or can be prepared by a conventional method.

The compounds listed in the Tables below can be prepared by the processes described.

TABLE 1

| Compounds I in which A and B are each H, $R^3$ is $CH_2$—$CH_2$— and the radical $R^4$—$R^3$—CONH— is [on] *in* the para-position | | |
|---|---|---|
| $R^4$ | $R^1$ | $R^2$ |
| 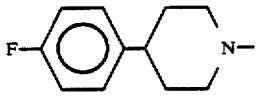 | H | H |
| 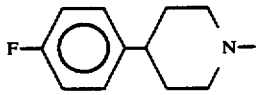 | $CH_3$ | H |
| 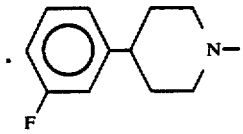 | —$CH_2$— | |
| 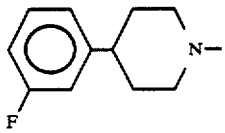 | H | H |
| 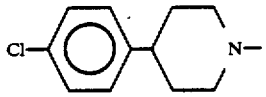 | —$CH_2$— | |

TABLE 1-continued
Compounds I in which A and B are each H, $R^3$ is $CH_2—CH_2—$ and the radical $R^4—R^3—CONH—$ is [on] *in* the para-position
| $R^4$ | $R^1$ | $R^2$ |
|---|---|---|
| 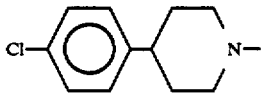 | $CH_3$ | H |
| 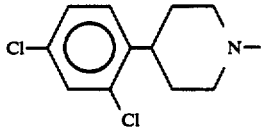 | $CH_3$ | H |
| 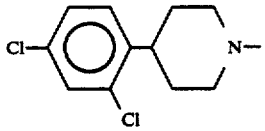 | $—CH_2—$ | |
| 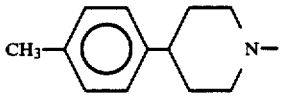 | H | H |
| 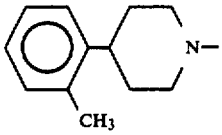 | $CH_3$ | H |
| 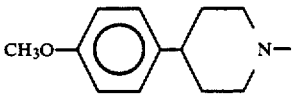 | $CH_3$ | H |
| 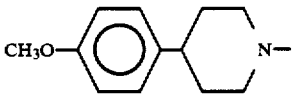 | $—CH_2—$ | |
| 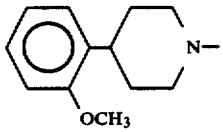 | $—CH_2CH_2—$ | |
| 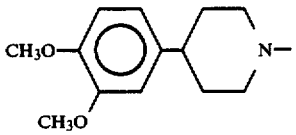 | $CH_3$ | H |
| 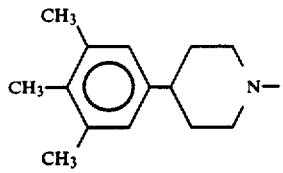 | $CH_3$ | H |

TABLE 1-continued
| Compounds I in which A and B are each H, $R^3$ is $CH_2—CH_2—$ and the radical $R^4—R^3—CONH—$ is [on] *in* the para-position | | |
|---|---|---|
| $R^4$ | $R^1$ | $R^2$ |
| 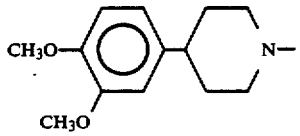 | $CH_3$ | H |
| 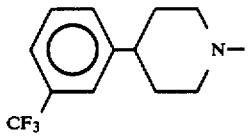 | $CH_3$ | H |
| 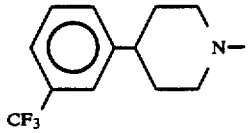 | H | H |
| 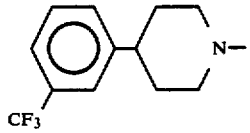 | $—CH_2—$ | |
| 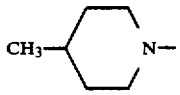 | $CH_3$ | H |
| 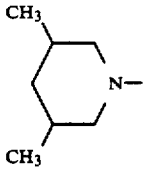 | $CH_3$ | H |
| 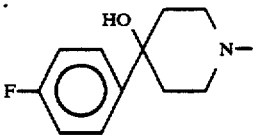 | $CH_3$ | H |
| 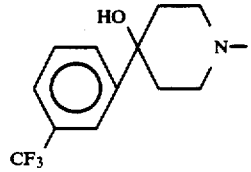 | H | H |
| 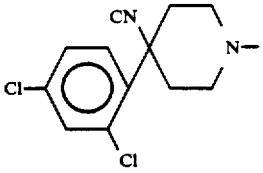 | $—CH_2—$ | |

TABLE 1-continued
| Compounds I in which A and B are each H, $R^3$ is $CH_2—CH_2—$ and the radical $R^4—R^3—CONH—$ is [on] *in* the para-position | | |
|---|---|---|
| $R^4$ | $R^1$ | $R^2$ |
| 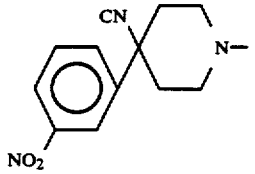 | H | H |
| 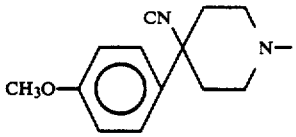 | $CH_3$ | H |
| 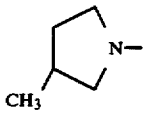 | $CH_3$ | H |
| 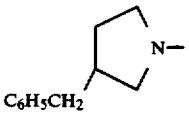 | H | H |
| 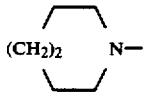 | $—CH_2—$ | |
| 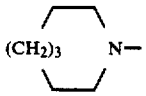 | $—CH_2—$ | |
| 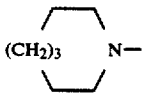 | $—CH_2—CH_2—CH_2—$ | |
| 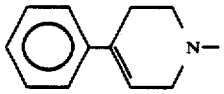 | $—CH_2—$ | |
| 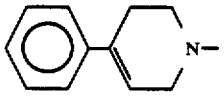 | $—CH_2CH_2—$ | |
| 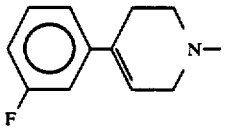 | $CH_3$ | H |
| 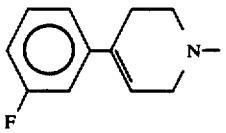 | H | H |

TABLE 1-continued
| Compounds I in which A and B are each H, $R^3$ is $CH_2—CH_2—$ and the radical $R^4—R^3—CONH—$ is [on] *in* the para-position | | |
|---|---|---|
| $R^4$ | $R^1$ | $R^2$ |
| 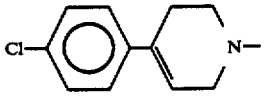 | $CH_3$ | H |
| 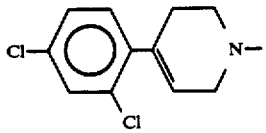 | $CH_3$ | H |
| 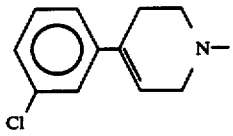 | $CH_3$ | H |
| 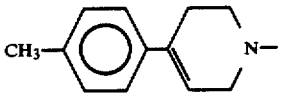 | $CH_3$ | H |
| 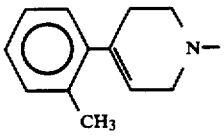 | H | H |
| 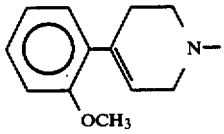 | $—CH_2—$ | |
| 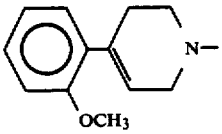 | $CH_3$ | H |
| 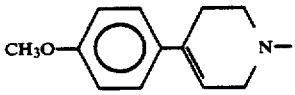 | $CH_3$ | H |
| 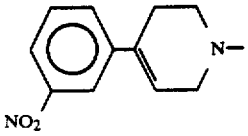 | $—CH_2—CH_2—$ | |
| 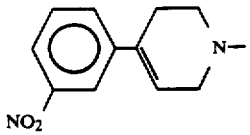 | $CH_3$ | H |

TABLE 1-continued
| Compounds I in which A and B are each H, $R^3$ is $CH_2—CH_2—$ and the radical $R^4—R^3—CONH—$ is [on] *in* the para-position | | |
|---|---|---|
| $R^4$ | $R^1$ | $R^2$ |
| 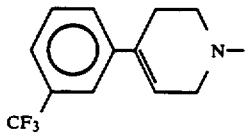 | $CH_3$ | H |
| 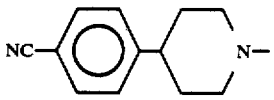 | $CH_3$ | H |
| 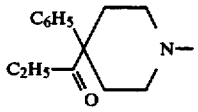 | $CH_3$ | H |
| 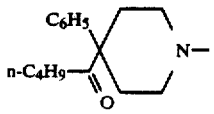 | $CH_3$ | H |
| 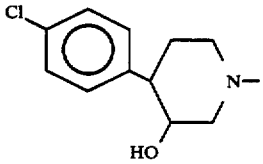 | $CH_3$ | H |
| 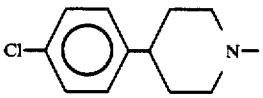 | H | H |
| 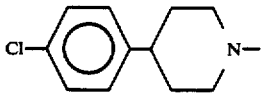 | $—CH_2—$ | |
| 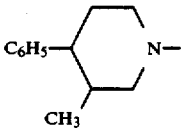 | $CH_3$ | H |
| 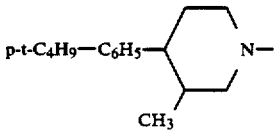 | $CH_3$ | H |
| 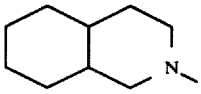 | $CH_3$ | H |
| 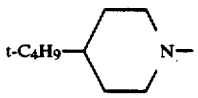 | $CH_3$ | H |

TABLE 1-continued
| Compounds I in which A and B are each H, $R^3$ is $CH_2—CH_2—$ and the radical $R^4—R^3—CONH—$ is [on] *in* the para-position | | |
|---|---|---|
| $R^4$ | $R^1$ | $R^2$ |
| 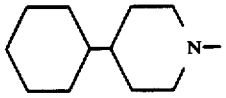 | $CH_3$ | H |
| 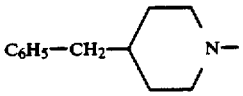 | $—CH_2—$ | |
| 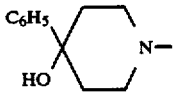 | H | H |
| 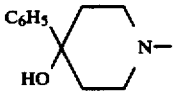 | $—CH_2—$ | |
| 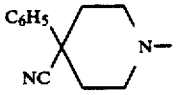 | H | H |
| 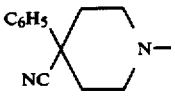 | $—CH_2—$ | |
| 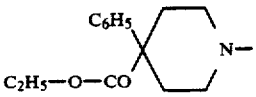 | $—CH_2—$ | |
| 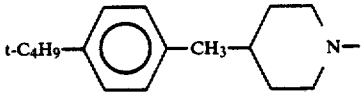 | $CH_3$ | H |
| 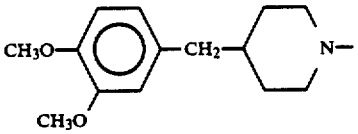 | $CH_3$ | H |
| 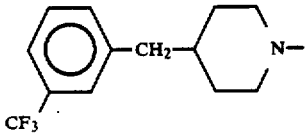 | $CH_3$ | H |
| 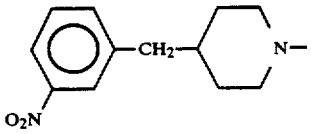 | $CH_3$ | H |
| 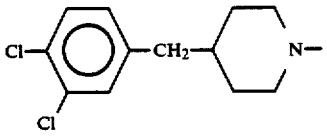 | $CH_3$ | H |

TABLE 1-continued
| Compounds I in which A and B are each H, $R^3$ is $CH_2—CH_2—$ and the radical $R^4—R^3—CONH—$ is [on] *in* the para-position | | |
|---|---|---|
| $R^4$ | $R^1$ | $R^2$ |
| 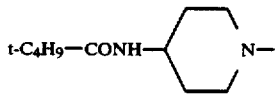 | $CH_3$ | H |
| 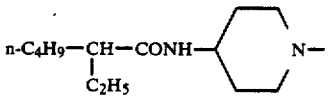 | $CH_3$ | H |
| 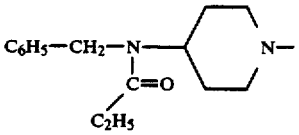 | $CH_3$ | H |
| 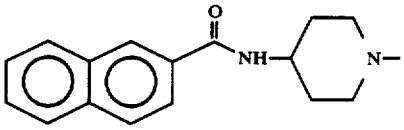 | $CH_3$ | H |
| 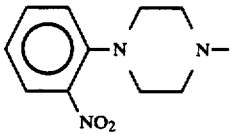 | $CH_3$ | H |
| 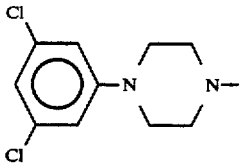 | $CH_3$ | H |
| 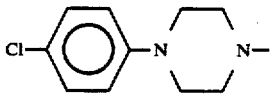 | $—CH_2—$ | |
| 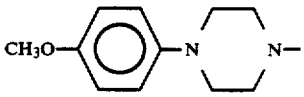 | $CH_3$ | H |
| 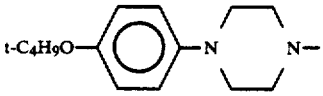 | $CH_3$ | H |
| 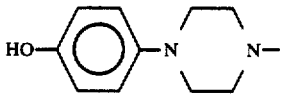 | $CH_3$ | H |
| 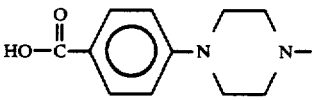 | $CH_3$ | H |

TABLE 1-continued
| Compounds I in which A and B are each H, $R^3$ is $CH_2—CH_2—$ and the radical $R^4—R^3—CONH—$ is [on] *in* the para-position | | |
|---|---|---|
| $R^4$ | $R^1$ | $R^2$ |
| 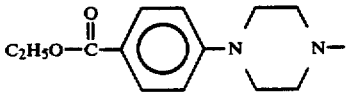 | $CH_3$ | H |
| 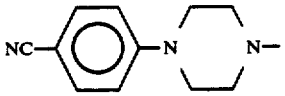 | $CH_3$ | H |
| 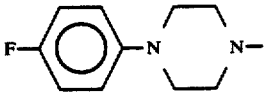 | H | H |
| 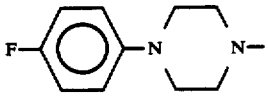 | $—CH_2—$ | |
| 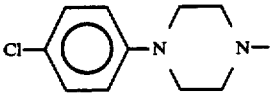 | $CH_3$ | H |
| 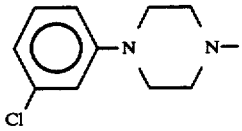 | $—CH_2—$ | |
| 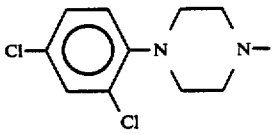 | H | H |
| 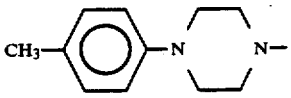 | $CH_3$ | H |
| 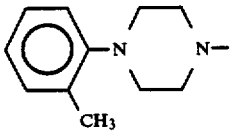 | $CH_3$ | H |
| 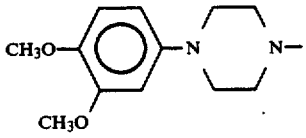 | $—CH_2—$ | |
| 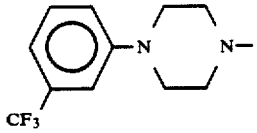 | H | H |

TABLE 1-continued
| Compounds I in which A and B are each H, $R^3$ is $CH_2—CH_2—$ and the radical $R^4—R^3—CONH—$ is [on] *in* the para-position | | |
|---|---|---|
| $R^4$ | $R^1$ | $R^2$ |
| 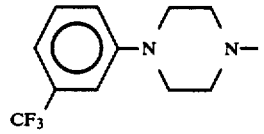 | $CH_3$ | H |
| 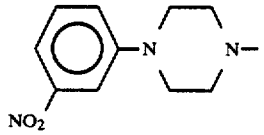 | H | H |
| 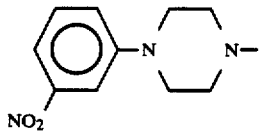 | $CH_3$ | H |
| 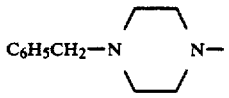 | H | H |
| 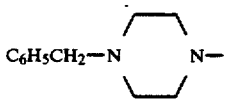 | $—CH_2—$ | |
| 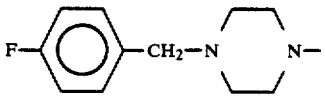 | H | H |
| 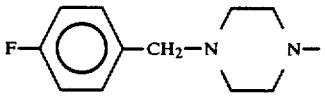 | $CH_3$ | H |
| 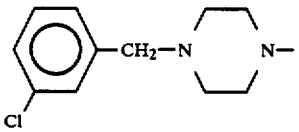 | $CH_3$ | H |
| 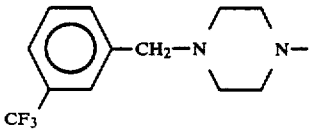 | $CH_3$ | H |
| 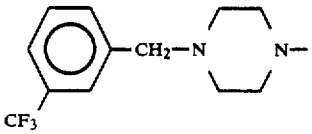 | $—CH_2—$ | |
| 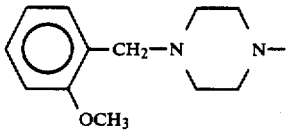 | $—CH_2—CH_2—CH_2CH_2—$ | |

TABLE 1-continued
| Compounds I in which A and B are each H, $R^3$ is $CH_2—CH_2—$ and the radical $R^4—R^3—CONH—$ is [on] *in* the para-position | | |
|---|---|---|
| $R^4$ | $R^1$ | $R^2$ |
| 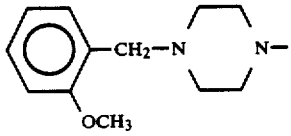 | $CH_3$ | H |
| 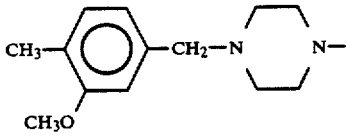 | H | H |
| 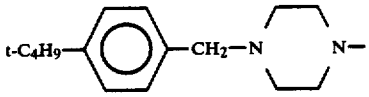 | $CH_3$ | H |
| 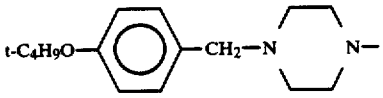 | $CH_3$ | H |
| 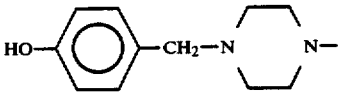 | $CH_3$ | H |
| 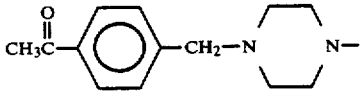 | $CH_3$ | H |
| 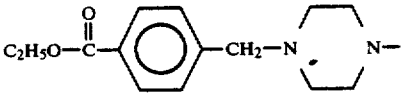 | $CH_3$ | H |
| 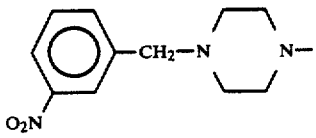 | $CH_3$ | H |
| 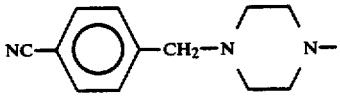 | $CH_3$ | H |
| 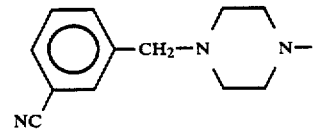 | $CH_3$ | H |
| 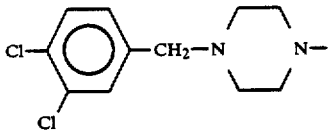 | $CH_3$ | H |

TABLE 1-continued
| Compounds I in which A and B are each H, $R^3$ is $CH_2—CH_2—$ and the radical $R^4—R^3—CONH—$ is [on] *in* the para-position | | |
|---|---|---|
| $R^4$ | $R^1$ | $R^2$ |
| 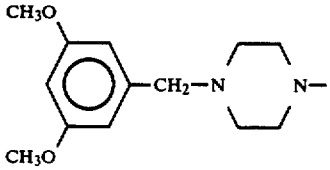 | $CH_3$ | H |
| 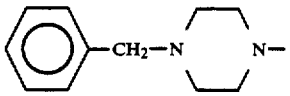 | $—CH_2—$ | |
| 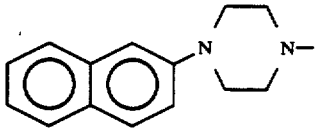 | $CH_3$ | H |
| 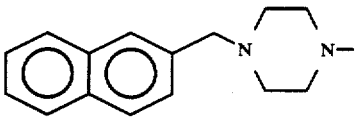 | $CH_3$ | H |
| 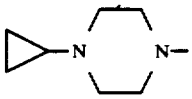 | $CH_3$ | H |
| 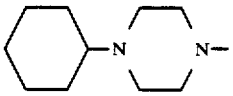 | $CH_3$ | H |
| 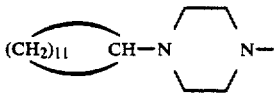 | $CH_3$ | H |
| 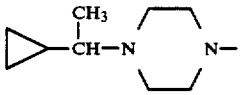 | $CH_3$ | H |
| 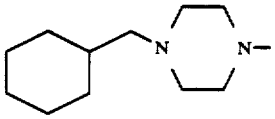 | $CH_3$ | H |
| 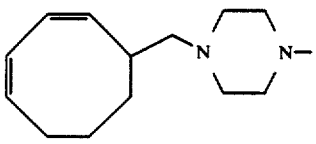 | $CH_3$ | H |
| 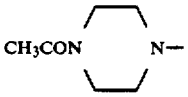 | $CH_3$ | H |

TABLE 1-continued
| Compounds I in which A and B are each H, $R^3$ is $CH_2$—$CH_2$— and the radical $R^4$—$R^3$—CONH— is [on] *in* the para-position | | |
|---|---|---|
| $R^4$ | $R^1$ | $R^2$ |
| 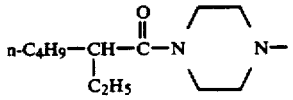 | $CH_3$ | H |
| 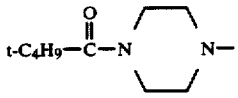 | $CH_3$ | H |
| 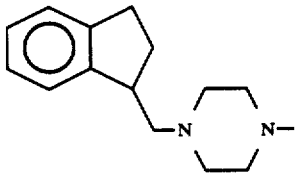 | $CH_3$ | H |
| 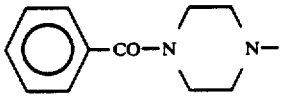 | $CH_3$ | H |
| 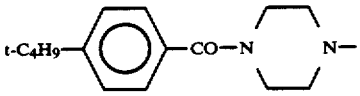 | $CH_3$ | H |
| 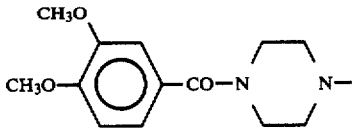 | $CH_3$ | H |
| 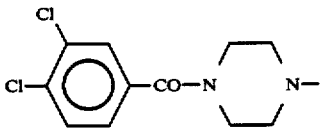 | $CH_3$ | H |
| 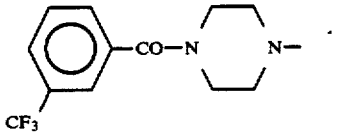 | $CH_3$ | H |
| 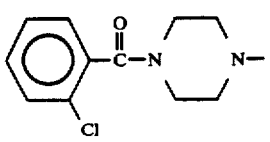 | $CH_3$ | H |
| 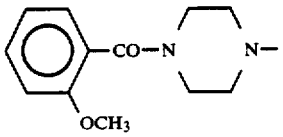 | $CH_3$ | H |
| 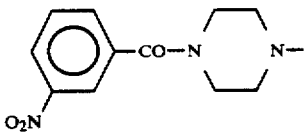 | $CH_3$ | H |

TABLE 1-continued
| Compounds I in which A and B are each H, $R^3$ is $CH_2—CH_2—$ and the radical $R^4—R^3—CONH—$ is [on] *in* the para-position | | |
|---|---|---|
| $R^4$ | $R^1$ | $R^2$ |
| 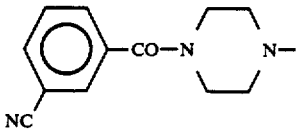 | $CH_3$ | H |
| 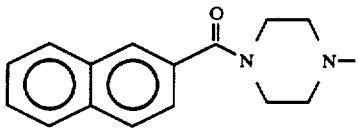 | $CH_3$ | H |
| 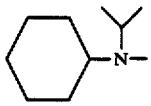 | $CH_3$ | H |
| 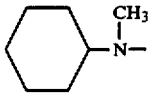 | $CH_3$ | H |
| 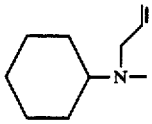 | $CH_3$ | H |
| 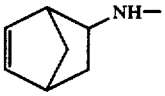 | $CH_3$ | H |
| 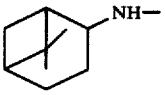 | $CH_3$ | H |
| 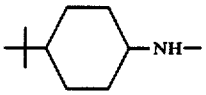 | $CH_3$ | H |
| $(C_6H_5)_2CH—NH—$ | $CH_3$ | H |
| $(C_6H_5)_2CHCH_2—NH—$ | $CH_3$ | H |
| $(C_6H_5)_2CH—CH_2—CH_2—NH—$ | $CH_3$ | H |
| $C_6H_5—CH_2—CH(C_6H_5)—NH—$ | $CH_3$ | H |
| $C_6H_5—CH(CH_3)—CH_2—NH—$ | $CH_3$ | H |
| $C_6H_5CH_2CH_2CH_2—N(CH_3)—$ | $CH_3$ | H |
| $C_6H_5—CH_2—CH_2—CH(CH_3)—NH—$ | $CH_3$ | H |

TABLE 1-continued
| Compounds I in which A and B are each H, $R^3$ is $CH_2—CH_2—$ and the radical $R^4—R^3—CONH—$ is [on] *in* the para-position | | |
|---|---|---|
| $R^4$ | $R^1$ | $R^2$ |
| 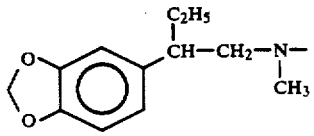 | $CH_3$ | H |
| $C_6H_5—CH(CH_3)—CH_2—CH(CH_3)—N(CH_3)—$ | $CH_3$ | H |
| 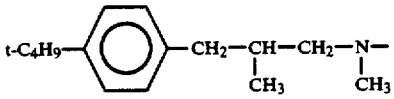 | $CH_3$ | H |
| $C_6H_5CH_2—CH_2—N(CH_3)—$ | $CH_3$ | H |
| 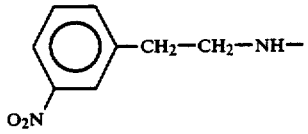 | $CH_3$ | H |
| 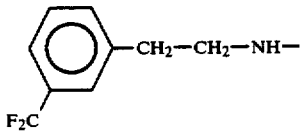 | $CH_3$ | H |
| 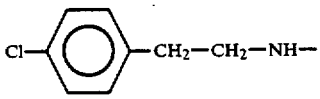 | $CH_3$ | H |
| 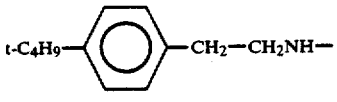 | $CH_3$ | H |
| 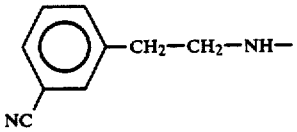 | $CH_3$ | H |
| 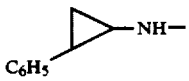 | $CH_3$ | H |
| $HC≡C—CH_2—N(CH_3)—$ | $CH_3$ | H |
| 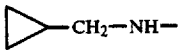 | $CH_3$ | H |
| 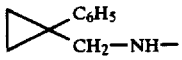 | $CH_3$ | H |

TABLE 1-continued
| Compounds I in which A and B are each H, $R^3$ is $CH_2—CH_2—$ and the radical $R^4—R^3—CONH—$ is [on] *in* the para-position | | |
|---|---|---|
| $R^4$ | $R^1$ | $R^2$ |
| 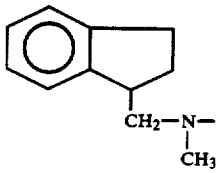 | $CH_3$ | H |
| 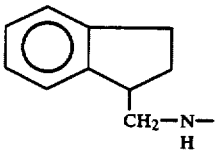 | $CH_3$ | H |
| 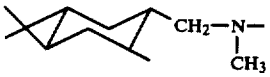 | $CH_3$ | H |
| 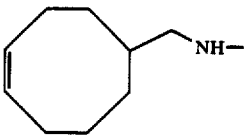 | $CH_3$ | H |
| 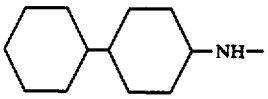 | $CH_3$ | H |
| [ 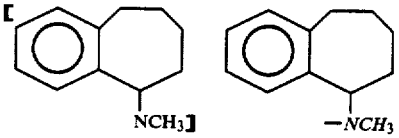 | $CH_3$ | H |
| 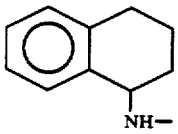 | $CH_3$ | H |
| [ 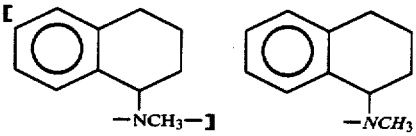 | $CH_3$ | H |
| 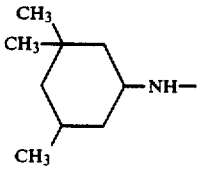 | $CH_3$ | H |
| [ 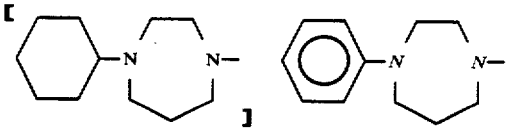 | H | H |

TABLE 1-continued
| Compounds I in which A and B are each H, $R^3$ is $CH_2—CH_2—$ and the radical $R^4—R^3—CONH—$ is [on] *in* the para-position | | |
|---|---|---|
| $R^4$ | $R^1$ | $R^2$ |
| [ 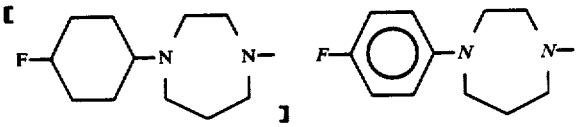 ] | $CH_3$ | H |
| [ 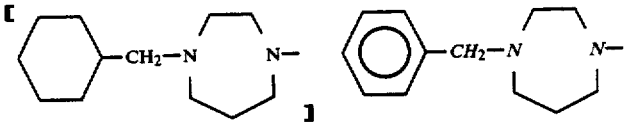 ] | H | H |
| $C_6H_5CH_2CH_2—NH—$ | $CH_3$ | H |
| 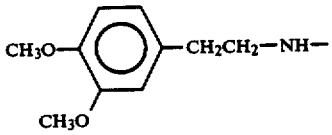 | $CH_3$ | H |
| cyclo-$C_3H_5—NH—$<br>cyclo-$C_6H_{11}—NH—$ | $CH_3$ | H |
| 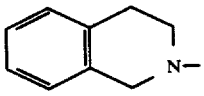 | $—CH_2—$<br>$—CH_2—$ | |
| 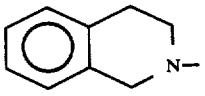 | $—CH_2CH_2—$ | |
| 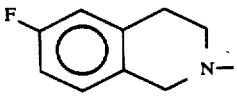 | H | H |
| 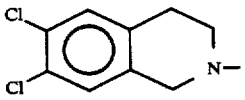 | $CH_3$ | H |
| 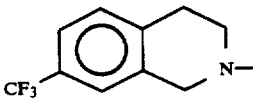 | $CH_3$ | H |
| $(n\text{-}C_8H_{17})_2N—$<br>$(n\text{-}C_4H_9)_2N—$ | $CH_3$ | H |
| 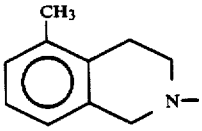 | $—CH_2—$<br>$—CH_2—$ | |
| 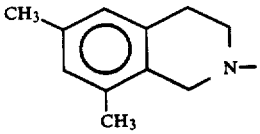 | $CH_3$ | H |

TABLE 1-continued
| Compounds I in which A and B are each H, $R^3$ is $CH_2$—$CH_2$— and the radical $R^4$—$R^3$—CONH— is [on] *in* the para-position | | |
|---|---|---|
| $R^4$ | $R^1$ | $R^2$ |
| 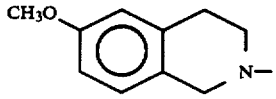 | $CH_3$ | H |
| 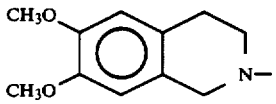 | H | H |
| 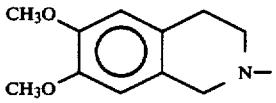 | $CH_3$ | H |
| 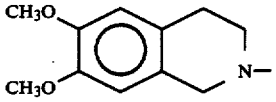 | —$CH_2$— | |
| 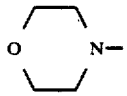 | $CH_3$ | H |
| 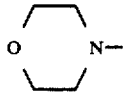 | —$CH_2$— | |
| 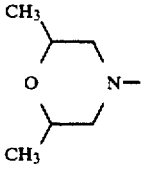 | $CH_3$ | H |
| 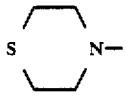 | —$CH_2$— | |
| 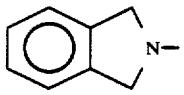 | $CH_3$ | H |
| 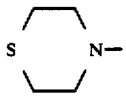 | $CH_3$ | H |
| 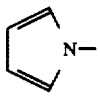 | $CH_3$ | H |
| 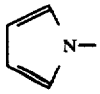 | H | H |

TABLE 1-continued
| Compounds I in which A and B are each H, $R^3$ is $CH_2$—$CH_2$— and the radical $R^4$—$R^3$—CONH— is [on] *in* the para-position | | |
|---|---|---|
| $R^4$ | $R^1$ | $R^2$ |
| 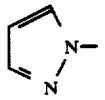 | $CH_3$ | H |
| 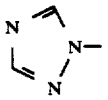 | $CH_3$ | H |
| 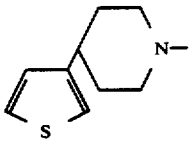 | $CH_3$ | H |
| 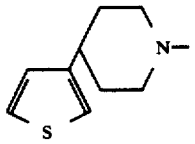 | H | H |
| 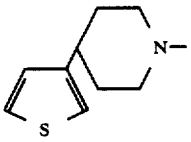 | —$CH_2$— | |
| 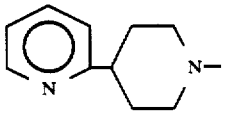 | —$CH_2$— | |
| 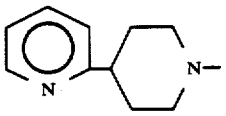 | $CH_3$ | H |
| 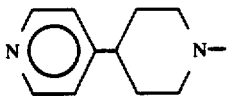 | $CH_3$ | H |
| 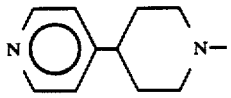 | —$CH_2$— | |
| 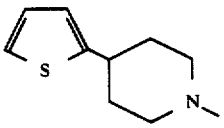 | $CH_3$ | H |
| 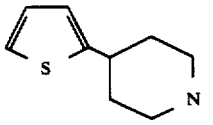 | H | H |

TABLE 1-continued
| Compounds I in which A and B are each H, $R^3$ is $CH_2—CH_2—$ and the radical $R^4—R^3—CONH—$ is [on] *in* the para-position | | |
|---|---|---|
| $R^4$ | $R^1$ | $R^2$ |
| 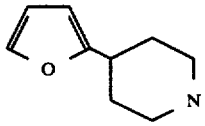 | $CH_3$ | H |
| 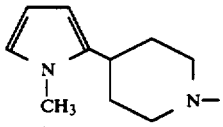 | $CH_3$ | H |
| 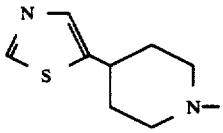 | $CH_3$ | H |
| 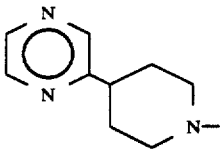 | $CH_3$ | H |
| 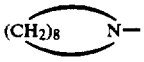 | H | H |
| 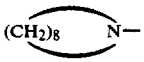 | $CH_3$ | H |
| 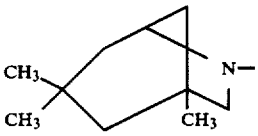 | $CH_3$ | H |
| 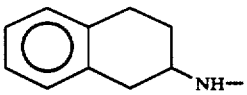 | $CH_3$ | H |
| 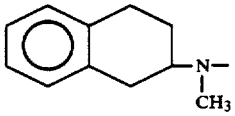 | $CH_3$ | H |
| 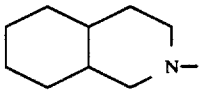 | $—CH_2—$ | |
| 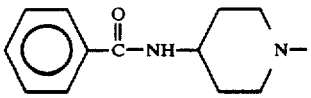 | $—CH_2—$ | |

TABLE 1-continued
| Compounds I in which A and B are each H, $R^3$ is $CH_2—CH_2—$ and the radical $R^4—R^3—CONH—$ is [on] *in* the para-position | | |
|---|---|---|
| $R^4$ | $R^1$ | $R^2$ |
| 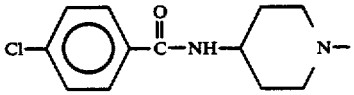 | $CH_3$ | H |
| 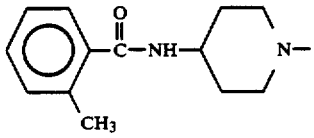 | $CH_3$ | H |
| 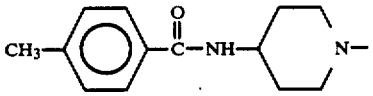 | $CH_3$ | H |
| 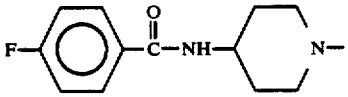 | $CH_3$ | H |
| 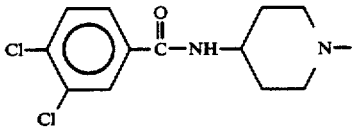 | $CH_3$ | H |
| 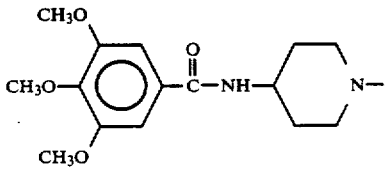 | $CH_3$ | H |
| 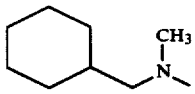 | $CH_3$ | H |
| 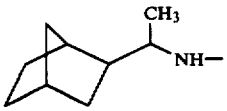 | $CH_3$ | H |
| 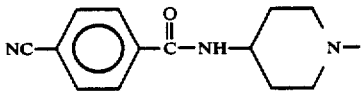 | $CH_3$ | H |
| 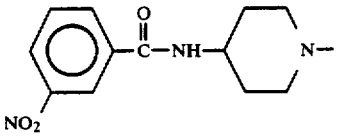 | $CH_3$ | H |
| 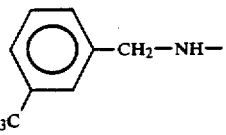 | $CH_3$ | H |

TABLE 1-continued
| Compounds I in which A and B are each H, $R^3$ is $CH_2—CH_2—$ and the radical $R^4—R^3—CONH—$ is [on] *in* the para-position | | |
|---|---|---|
| $R^4$ | $R^1$ | $R^2$ |
| 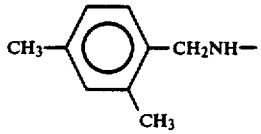 | $CH_3$ | H |
| 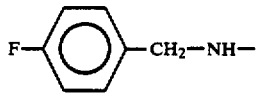 | $CH_3$ | H |
| 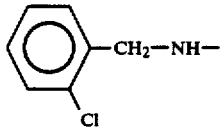 | $CH_3$ | H |
| 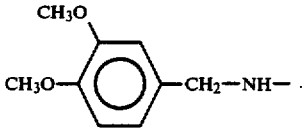 | $CH_3$ | H |
| 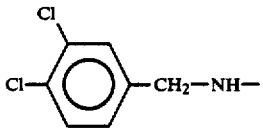 | $CH_3$ | H |
| 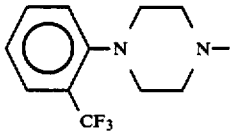 | $CH_3$ | H |
| 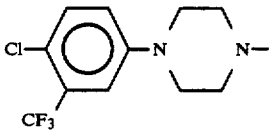 | $CH_3$ | H |
| 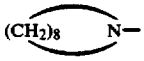 | $CH_3$ | H |
| 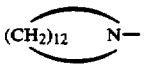 | H | H |
| 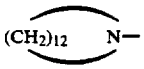 | $CH_3$ | H |
| 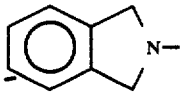 | $CH_3$ | H |

TABLE 1-continued
| Compounds I in which A and B are each H, $R^3$ is $CH_2$—$CH_2$— and the radical $R^4$—$R^3$—CONH— is [on] *in* the para-position | | |
|---|---|---|
| $R^4$ | $R^1$ | $R^2$ |
| 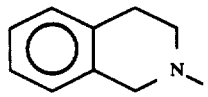 | $CH_3$ | H |
| n-$C_8H_{17}$—N(CH$_3$)— | $CH_3$ | H |
| n-$C_6H_{13}$—N(CH$_3$)— | $CH_3$ | H |
| 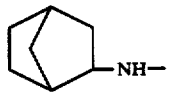 | $CH_3$ | H |
| 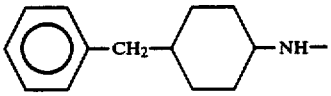 | $CH_3$ | H |
| 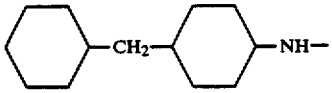 | $CH_3$ | H |
| 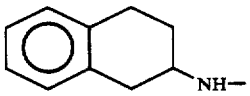 | $CH_3$ | H |
| 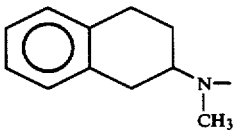 | $CH_3$ | H |
| 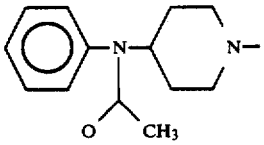 | $CH_3$ | H |
| 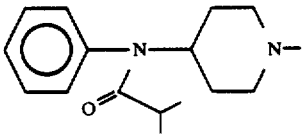 | $CH_3$ | H |
| 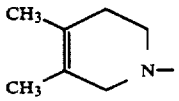 | $CH_3$ | H |
| 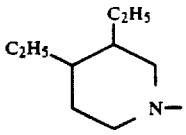 | $CH_3$ | H |

TABLE 1-continued

| Compounds I in which A and B are each H, $R^3$ is $CH_2—CH_2—$ and the radical $R^4—R^3—CONH—$ is [on] *in* the para-position | | |
|---|---|---|
| $R^4$ | $R^1$ | $R^2$ |
| 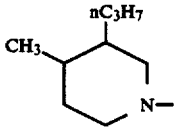 | $CH_3$ | H |

TABLE 2

| Compounds I in which A and B are each H, $R^3$ is $—CH_2—\underset{\underset{CH_3}{\vert}}{CH}—$ and the radical $R^4—R^3—CO—NH$ is in the para-position | | |
|---|---|---|
| $R^4$ | $R^1$ | $R^2$ |
| 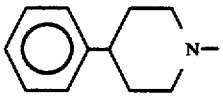 | $CH_3$ | H |
| 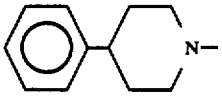 | H | H |
| 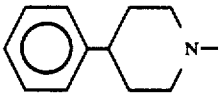 | $—CH_2—$ | |
| 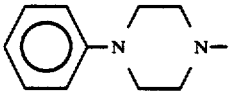 | $CH_3$ | H |
| 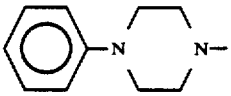 | H | H |
| 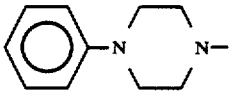 | $—CH_2—$ | |
| 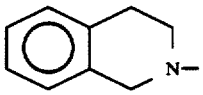 | $CH_3$ | H |
| [ 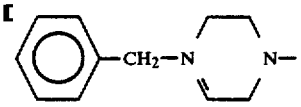 | $CH_3$ | H] |
| 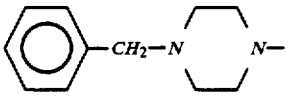 | *$CH_3$* | *H* |
| 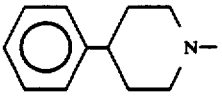 | $CH_3$ | H |

TABLE 2-continued

| Compounds I in which A and B are each H, $R^3$ is $—CH_2—\underset{\underset{CH_3}{\vert}}{CH}—$ and the radical $R^4—R^3—CO—NH$ is in the para-position | | |
|---|---|---|
| $R^4$ | $R^1$ | $R^2$ |
| 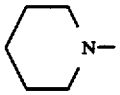 | H | H |

TABLE 3

| Compounds I in which A and B are each H, $R^3$ is $—\overset{\overset{CH_3}{\vert}}{CH}—$ and the radical $R^4—R^3—CONH$ is in the para-position | | |
|---|---|---|
| $R^4$ | $R^1$ | $R^2$ |
| 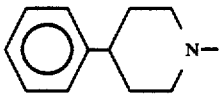 | $—CH_3$ | H |
| 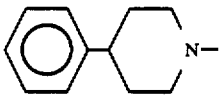 | $—CH_2—$ | |
| 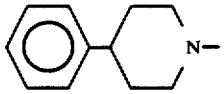 | $—CH_2—CH_2—$ | |
| 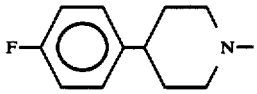 | $—CH_3$ | H |
| 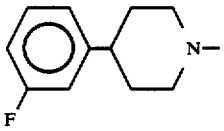 | $—CH_3$ | H |
| 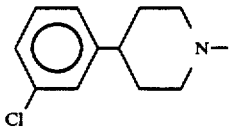 | $—CH_3$ | H |
| 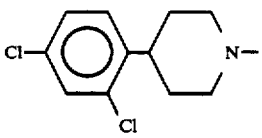 | $—CH_3$ | H |

TABLE 3-continued

Compounds I in which A and B are each H, $R^3$ is $-\overset{CH_3}{\overset{|}{C}}H-$ and the radical $R^4-R^3-CONH$ is in the para-position

| $R^4$ | $R^1$ | $R^2$ |
|---|---|---|
| 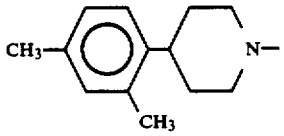 | $-CH_2-$ | |
| 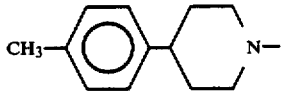 | $-CH_3$ | H |
| 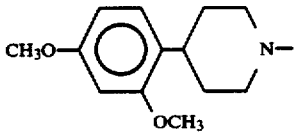 | $-CH_3$ | H |
| 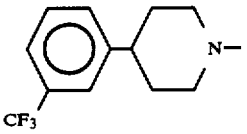 | $-CH_3$ | H |
| 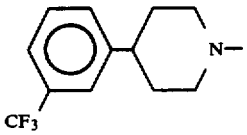 | $-CH_2-$ | |
| 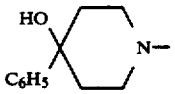 | $CH_3$ | H |
| 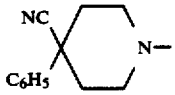 | $-CH_2-$ | |
| 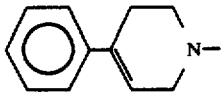 | $CH_3$ | H |
| 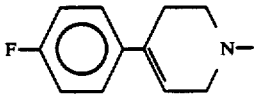 | $CH_3$ | H |
| 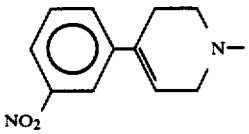 | $-CH_2-$ | |
| 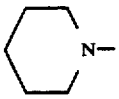 | $CH_3$ | H |

TABLE 3-continued

Compounds I in which A and B are each H, $R^3$ is $-\overset{CH_3}{\overset{|}{C}}H-$ and the radical $R^4-R^3-CONH$ is in the para-position

| $R^4$ | $R^1$ | $R^2$ |
|---|---|---|
| 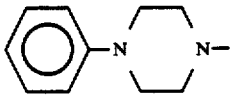 | $CH_3$ | H |
| 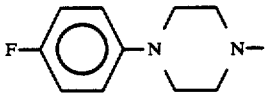 | $CH_3$ | H |
| 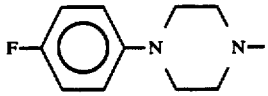 | $-CH_2-$ | |
| 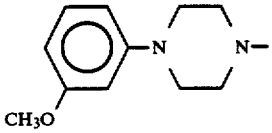 | $CH_3$ | H |
| 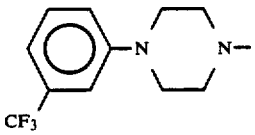 | $CH_3$ | H |
| 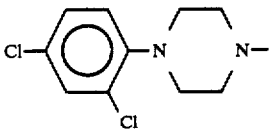 | $CH_3$ | H |
| 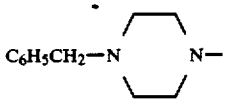 | $CH_3$ | H |
| 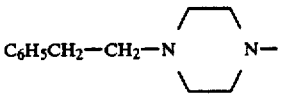 | $CH_3$ | H |
| cyclo-$C_6H_{11}$—NH— | $CH_3$ | H |
| 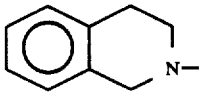 | $CH_3$ | H |
| 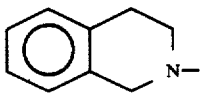 | $-CH_2-$ | |
| 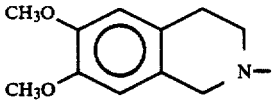 | $CH_3$ | H |

TABLE 3-continued

Compounds I in which A and B are each H, $R^3$ is $-\overset{CH_3}{\overset{|}{C}}H-$ and the radical $R^4-R^3-CONH$ is in the para-position

| $R^4$ | $R^1$ | $R^2$ |
|---|---|---|
| 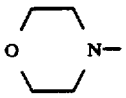 | $CH_3$ | H |

TABLE 4

Compounds I in which A and B are each H, $R^3$ is $-CH_2-$, and the radical $R^4-R^3-CONH-$ is in the para-position

| $R^4$ | $R^1$ | $R^2$ |
|---|---|---|
| 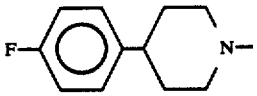 | $CH_3$ | H |
| 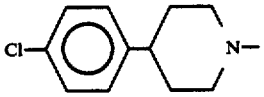 | $-CH_2-$ | |
| 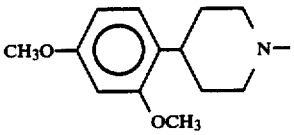 | $CH_3$ | H |
| 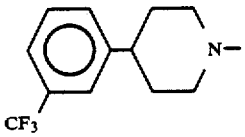 | $CH_3$ | H |
| 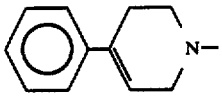 | $CH_3$ | H |
| 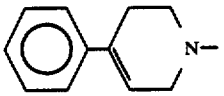 | $-CH_2-$ | |
| 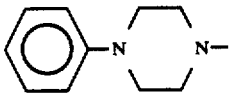 | $CH_3$ | H |
| 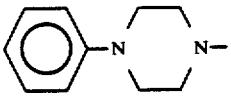 | $-CH_2-$ | |
| 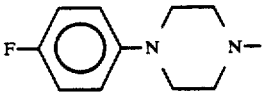 | $CH_3$ | H |
| 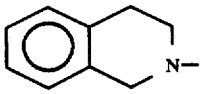 | $CH_3$ | H |

TABLE 4-continued

Compounds I in which A and B are each H, $R^3$ is $-CH_2-$, and the radical $R^4-R^3-CONH-$ is in the para-position

| $R^4$ | $R^1$ | $R^2$ |
|---|---|---|
| 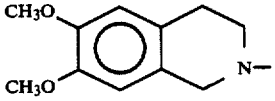 | $CH_3$ | H |
| 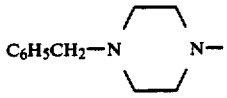 | $CH_3$ | H |
| 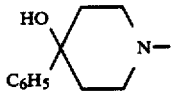 | $CH_3$ | H |
| 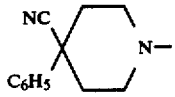 | $CH_3$ | H |

TABLE 5

Compounds I in which A and B are each H, $R^3$ is $-CH_2CH_2CH_2-$, and the radical $R^4-R^3-CONH$ is in the para-position

| $R^4$ | $R^1$ | $R^2$ |
|---|---|---|
| 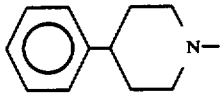 | $-CH_2CH_2-$ | |
| 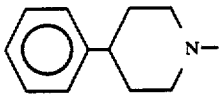 | $-CH_2CH_2CH_2-$ | |
| 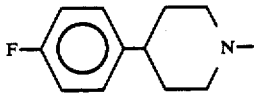 | $CH_3$ | H |
| 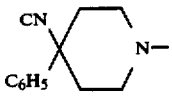 | $CH_3$ | H |
| 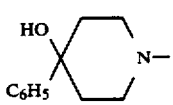 | $-CH_2-$ | |
| 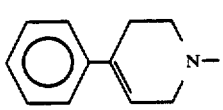 | $CH_3$ | H |
| 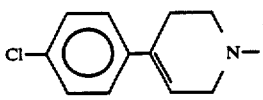 | H | H |

TABLE 5-continued

Compounds I in which A and B are each H, $R^3$ is $-CH_2CH_2CH_2-$, and the radical $R^4-R^3-CONH$ is in the para-position

| $R^4$ | $R^1$ | $R^2$ |
|---|---|---|
| 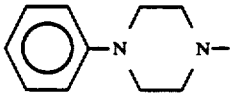 | $CH_3$ | H |
| 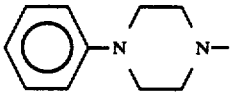 | H | H |
| 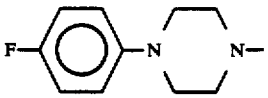 | $CH_3$ | H |
| 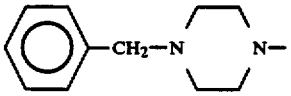 | $CH_3$ | H |
| 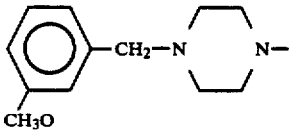 | | $-CH_2-$ |
| 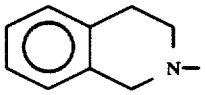 | $CH_3$ | H |
| 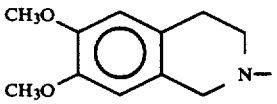 | $CH_3$ | H |
| $C_6H_5CH_2-N(CH_3)-$ | $CH_3$ | H |
| $C_6H_5CH_2NH-$ | $CH_3$ | H |
| 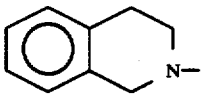 | $CH_3$ | H |
| 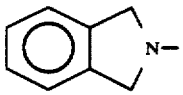 | $CH_3$ | H |
| 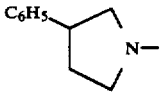 | $CH_3$ | H |
| $C_6H_5-CH_2-N(\text{iso-propyl})-$ | $CH_3$ | H |

TABLE 6

Compounds I in which A and B are each H, $R^3$ is $-(CH_2)_4-$, and the radical $R^4-R^3-CONH$ is in the para-position

| $R^4$ | $R^1$ | $R^2$ |
|---|---|---|
| 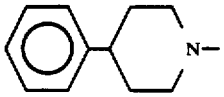 | $CH_3$ | H |
| 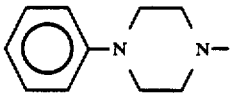 | $CH_3$ | H |
| 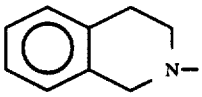 | $CH_3$ | H |

TABLE 7

Compounds I in which A and B are each H, $R^3$ is $CH(CH_3)-CH_2-$, and the radical $R^4-R^3-CONH$ is in the para-position

| $R^4$ | $R^1$ | $R^2$ |
|---|---|---|
| 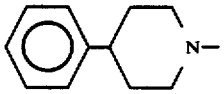 | H | H |
| 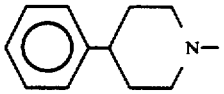 | $CH_3$ | H |
| 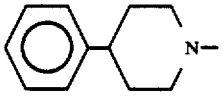 | | $-CH_2-$ |
| 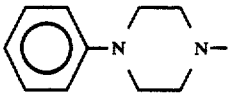 | $CH_3$ | H |
| 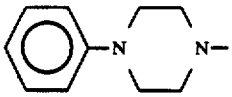 | H | H |
| 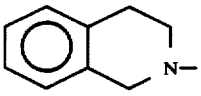 | H | H |
| 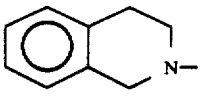 | $CH_3$ | H |
| 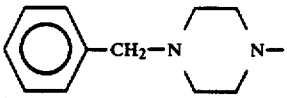 | $CH_3$ | H |

TABLE 8

Compounds I in which A and B are each H, R is $-\overset{C_2H_5}{\overset{|}{CH}}-$, and the radical $R^4-R^3-CONH$ is in the para-position

| $R^4$ | $R^1$ | $R^2$ |
|---|---|---|
| 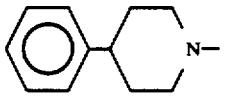 | H | H |
| 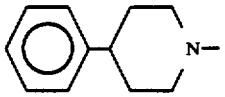 | $CH_3$ | H |
| 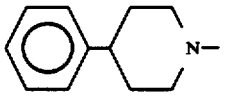 | $-CH_2-$ | |
| 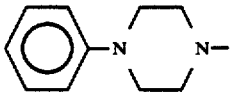 | H | H |
| 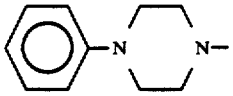 | $CH_3$ | H |
| 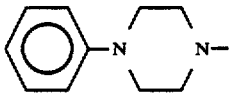 | $-CH_2-$ | |
| 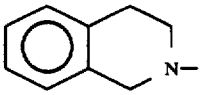 | $CH_3$ | H |
| 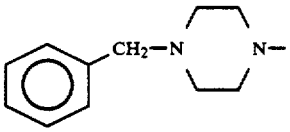 | $CH_3$ | H |

TABLE 9

Compounds I in which A and B are each H, $R^3$ is $\begin{array}{c} CH_3 \quad CH_3 \\ \diagdown \quad / \\ CH \\ | \\ -CH- \end{array}$, and the radical $R^4-R^3-CONH$ is in the para-position

| $R^4$ | $R^1$ | $R^2$ |
|---|---|---|
| 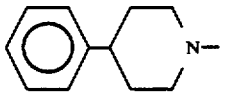 | H | H |
| 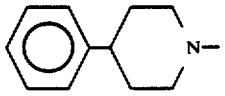 | $CH_3$ | H |
| 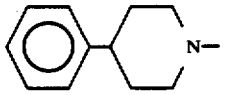 | $-CH_2-$ | |

TABLE 9-continued

Compounds I in which A and B are each H, $R^3$ is $\begin{array}{c} CH_3 \quad CH_3 \\ \diagdown \quad / \\ CH \\ | \\ -CH- \end{array}$, and the radical $R^4-R^3-CONH$ is in the para-position

| $R^4$ | $R^1$ | $R^2$ |
|---|---|---|
| 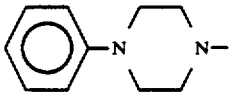 | H | H |
| 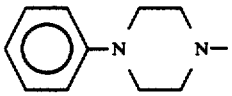 | $CH_3$ | H |
| 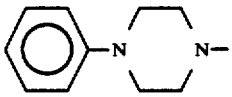 | $-CH_2-$ | |
| 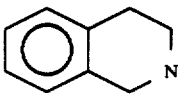 | $CH_3$ | H |
| 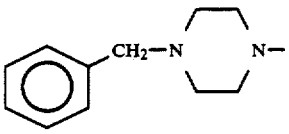 | $CH_3$ | H |

TABLE 10

Compounds I in which A and B are each H, $R^3$ is $-\overset{nC_3H_7}{\overset{|}{CH}}-$, and the radical $R^4-R^3-CONH$ is in the para-position

| $R^4$ | $R^1$ | $R^2$ |
|---|---|---|
| 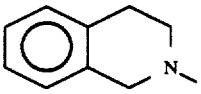 | H | H |
| 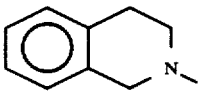 | $CH_3$ | H |
| 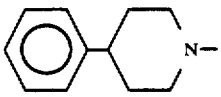 | H | H |
| 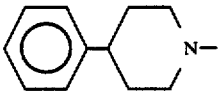 | $CH_3$ | H |
| 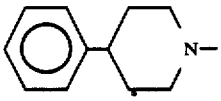 | $-CH_2-$ | |

TABLE 10-continued

Compounds I in which A and B are each H, $R^3$ is $-\overset{nC_3H_7}{\overset{|}{C}}H-$, and the radical $R^4-R^3-CONH$ is in the para-position

| $R^4$ | $R^1$ | $R^2$ |
|---|---|---|
| 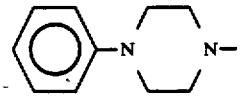 | $CH_3$ | H |
| 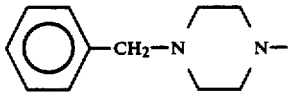 | $CH_3$ | H |

TABLE 11

Compounds I in which A and B together constitute a bond, $R^3$ is $-CH_2CH_2-$, and the radical $R^4-R^3-CONH$ is in the para-position

| $R^4$ | $R^1$ | $R^2$ |
|---|---|---|
| 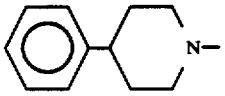 | H | H |
| 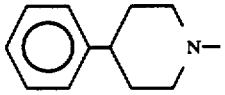 | H | $CH_3$ |
| 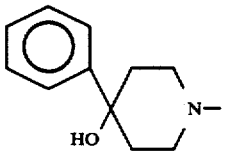 | H | H |
| 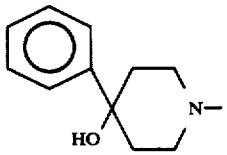 | H | $CH_3$ |
| 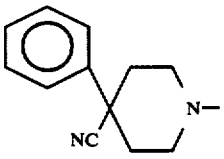 | H | H |
| 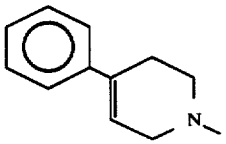 | H | H |
| 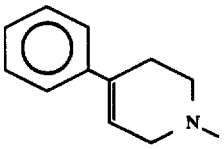 | H | $CH_3$ |

TABLE 11-continued

Compounds I in which A and B together constitute a bond, $R^3$ is $-CH_2CH_2-$, and the radical $R^4-R^3-CONH$ is in the para-position

| $R^4$ | $R^1$ | $R^2$ |
|---|---|---|
| 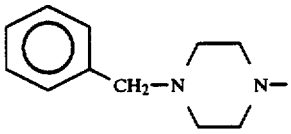 | H | H |
| $C_6H_5CH_2-CH_2-\overset{CH_3}{\overset{\vert}{N}}-$ | H | H |
| $C_6H_5CH_2-CH_2-\overset{CH_3}{\overset{\vert}{N}}-$ | H | $CH_3$ |
| 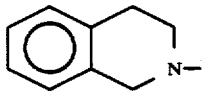 | H | H |

TABLE 12

Compounds I in which A and B together constitute a bond, $R^3$ is $-\overset{CH_3}{\overset{|}{C}}H-$, and the radical $R^4-R^3-CONH$ is in the para-position

| $R^4$ | $R^1$ | $R^2$ |
|---|---|---|
| 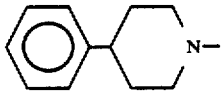 | H | H |
| 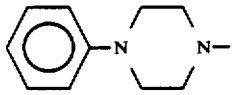 | H | H |
| 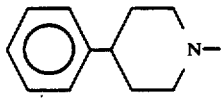 | H | $CH_3$ |
| 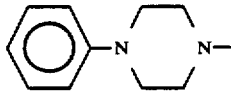 | H | $CH_3$ |
| 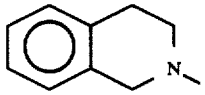 | H | H |
| $C_6H_5CH_2-N$ 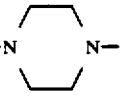 | H | H |
| 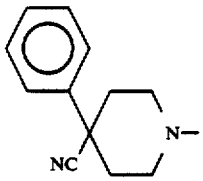 | H | H |

TABLE 12-continued

Compounds I in which A and B together constitute a bond, $R^3$ is $-\overset{CH_3}{\overset{|}{C}}H-$, and the radical $R^4-R^3-CONH$ is in the para-position

| $R^4$ | $R^1$ | $R^2$ |
|---|---|---|
| 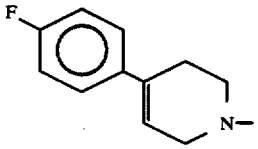 | H | H |

TABLE 13

Compounds I in which A and B together constitute a bond, $R^3$ is $-(CH_2)_3-$, and the radical $R^4-R^3-CONH$ is in the para-position

| $R^4$ | $R^1$ | $R^2$ |
|---|---|---|
| 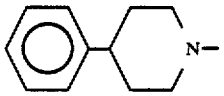 | H | H |
| 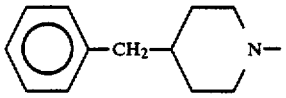 | H | H |
| 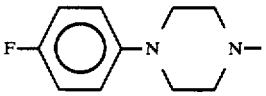 | H | H |
| 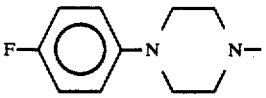 | H | $CH_3$ |
| 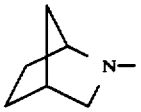 | H | H |
| 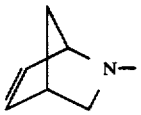 | H | H |
| 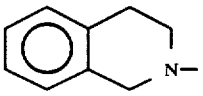 | H | H |
| 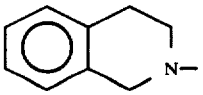 | H | $CH_3$ |

TABLE 14

Compounds I in which A and B are each H, $R^3$ is $-CH_2CH_2-$, and the radical $R^4-R^3-CONH$ is in the meta-position

| $R^4$ | $R^1$ | $R^2$ |
|---|---|---|
| 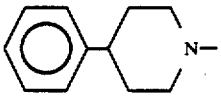 | | $-CH_2-$ |
| 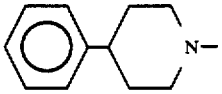 | | $-CH_2CH_2-$ |
| 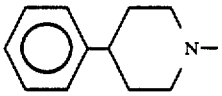 | H | H |
| 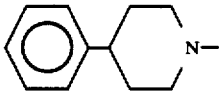 | $CH_3$ | H |
| 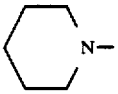 | $CH_3$ | H |
| 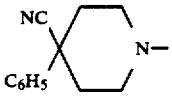 | $CH_3$ | H |
| 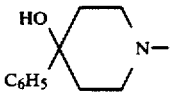 | $CH_3$ | H |
| 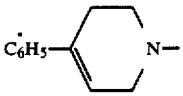 | $CH_3$ | H |
| 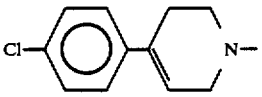 | $CH_3$ | H |
| 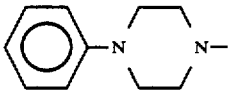 | $CH_3$ | H |
| 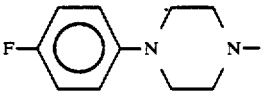 | $CH_3$ | H |
| 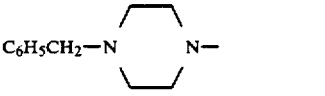 | $CH_3$ | H |
| 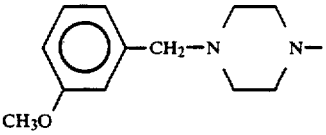 | $CH_3$ | H |

TABLE 14-continued

Compounds I in which A and B are each H, $R^3$ is $-CH_2CH_2-$, and the radical $R^4-R^3-CONH$ is in the meta-position

| $R^4$ | $R^1$ | $R^2$ |
|---|---|---|
| 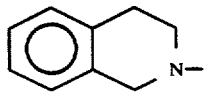 | $CH_3$ | H |
| 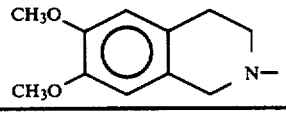 | $CH_3$ | H |

TABLE 15

Compounds I in which A andB are each H, $R^3$ is $-\overset{CH_3}{\overset{|}{C}}H-$, and the radical $R^4-R^3-CONH$ is in the meta-position

| $R^4$ | $R^1$ | $R^2$ |
|---|---|---|
| 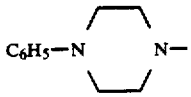 | $CH_3$ | H |
| 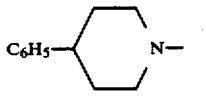 | $-CH_2-$ | |
| 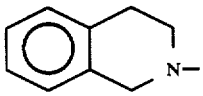 | $CH_3$ | H |
| 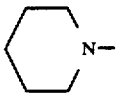 | $-CH_2-$ | |
| 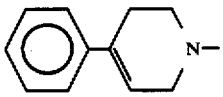 | H | H |

Compounds I in which A, B and $R^2$ are each hydrogen and $R^1$ is not hydrogen (4,5-dihydro-3(2H)-pyridazinones) have an asymmetric carbon atom in the 5-position and are therefore normally obtained in the form of their racemates. The present invention also relates to the enantiomers; advantageously, resolution is effected at the stage of compound IX (if in this compound A, B and $R^2$ are each hydrogen) in a conventional manner, for example by formation of diastereomeric salts with an optically active carboxylic acid, eg. dibenazoyltartaric acid or camphor-10-sulfonic acid, and the enantiomers are obtained by separate reaction of the resulting optically active precursors.

Compounds of the formula I in which $R^3$ is a substituted alkylene group can contain an asymmetric carbon atom in this alkylene chain. The present invention also relates to the enantiomers, which can be separated in a conventional manner, for example by formation of diastereomeric salts with an optically active carboxylic acid or sulfonic acid, or can be obtained by using appropriate optically active precursors, such as the compounds of the formulae VII, X and XI.

Furthermore, the compounds I can possess asymmetric carbon atoms in the amine moiety $R^4$. They are preferably prepared starting from the optically active amines VIII, by reaction with a compound VII or via the intermediates X or XI.

Compounds I in which $R^1$ and $R^2$ together form a methylene, ethylene, propylene or butylene group (3,4-diazabicyclo[4.1.0]heptenones, 3,4-diazabicyclo[4.2.0]octenones, 3,4-diazabicyclo[4.3.0]nonenones and 3,4-diazabicyclo[4.4.0]decanones) also form racemates, owing to the presence of the asymmetric carbon atoms 1 and 6 of the 3,4-diazabicyclo[4.n.0]alk-2-en-5-one ring. The present invention also relates to the enantiomers obtainable from these racemates.

In particular, the novel compounds of the formula I and their salts with a pharmaceutically tolerated acid inhibit thrombocyte aggregation and gastric secretion and have hypotensive and positively inotropic properties.

The following methods were used to examine the pharmacodynamic properties of the products according to the invention:

1. Inhibition of the collagen-induced aggregation of human thrombocytes in vitro.

Thrombocyte-rich plasma is obtained by centrifuging venous citrate blood (300 g, 10 minutes duration at 4° C.). Photometric measurement of the thrombocyte aggregation is carried out with the addition of $MgCl_2$ (final concentration 10 millimoles/liter) and of collagen Stago (final concentration 0.02 mg/ml) in a Born Mk 3 aggregometer. The maximum extinction change/sec. is used as a measure of the aggregation.

The aggregation-inhibiting activity of the substances is tested after an incubation time of 10 minutes.

The EC 50% is taken to be the concentration causing 50% inhibition of aggregation.

2. Hypotensive action on anesthetized rats.

To test the hypotensive effect, the substances are administered intraperitoneally or intravenously to groups of 3–5 male Sprague-Dawley rats weighing 240–280 g, under urethane anesthesia (1.78 mg/kg, administered intraperitoneally).

The measurement of the blood pressure in the carotid artery is carried out by means of Statham transducers. The ED 20% is determined as the dose which lowers the mean carotid blood pressure by 20%.

3. Inhibition of gastric secretion

Inhibition of the secretion of gastric acid results in an increase in the pH of the gastric mucous membrane. It is investigated on groups of 4 female Sprague-Dawley rats weighing 160–180 g. The animals fast for 48 hours (water ad libitum), and are pretreated with various doses (administered orally). After 1 hour, they are anesthetized with Na hexabarbital (46.4 mg/kg, administered intravenously), after which a pH electrode (Philips type CJP special electrode) is introduced into the stomach and the pH on the surfaace of the gastric mucous membrane is measured (pH for untreated animals: $1.40 \pm 0.002$; $N=200$). The ED 0.75, ie. the dose which increases the pH by an average of 0.75 compared with untreated control animals, is determined from the linear regression between the logarithms of the doses administered and of the increase in pH.

In these tests, the novel substances are effective in very low doses.

Accordingly, the present invention also relates to therapeutic agents or formulations which, in addition to conventional pharmaceutical excipients and diluents, contain a compound of the formula I or its salt as an active compound, and to the use of these compounds for therapeutic purposes.

The therapeutic agents or formulations can be prepared in a conventional manner by compounding an appropriate dose with the conventional excipients or diluents and the conventionally used pharmaceutical auxiliaries, in accordance with the desired route of administration. Suitable doses for man are from 0.1 to 100 mg, oral administration being preferred.

Examples of suitable forms for oral administration are tablets, film tablets, coated tablets, capsules, pills, powders, solutions, suspensions or depot forms.

For practical use, the compounds employed according to the invention are formulated with the excipients conventionally used in pharmaceutical production. For example, appropriate tablets can be obtained by mixing the active compound with conventional auxiliaries, for example inert diluents, such as dextrose, sugar, sorbitol, polyvinylpyrrolidone, mannitol, calcium carbonate, calcium phosphate or lactose, disintegrating agents, eg. corn starch, alginic acid or polyvinylpyrrolidone, binders, eg. starch or gelatine, lubricants, eg. magnesium stearate or talc, and/or agents for achieving a depot effect, eg. carboxypolymethylene, carboxymethylcellulose, cellulose acetate phthalate or polyvinyl acetate. The tablets can also consist of a plurality of layers (cf. H. Sucker et al, Pharmazeutische Technologie, Thieme Verlag, Stuttgart 1978).

Accordingly, coated tablets may be prepared by coating cores, prepared similarly to the tablets, with agents conventionally used in tablet coatings, eg. polyvinylpyrrolidone, shellac, gum arabic, talc, titanium dioxide or sugar. The tablet shell can also consist of several layers, in which the auxiliaries mentioned above in connection with the tablets may be used.

The Examples which follow illustrate the preparation of the novel 6-(acylaminoaryl)-3(2H)-pyridazinones.

EXAMPLE 1

5.8 g (20 millimoles) of 6-[p-(3-chloropropionylamino]-4,5-dihydro-3(2H)-pyridazinone were stirred with 3.5 g (25 millimoles) of potassium carbonate and 2.17 g (25 millimoles) of morpholine in 50 ml of dimethylformamide for 8 hours at 80° C. 500 g of ice/water were added, after which the crystals were filtered off under suction and recrystallized from dimethylformamide/water. The product was dried under greatly reduced pressure at 50° C. to give 5.4 g (82%) of 6-[p-3-(1-morpholino)-propionylaminophenyl]-B 4,5-dihydro-3(2H)-pyridazinone as colorless crystals of melting point 183°-185° C.

The compounds of Examples 2 to 104 were prepared similarly to Example 1. If the compounds are obtained in the form of oils, they can be purified by extraction with methylene chloride and/or column chromatography over silica gel or alumina using a methylene chloride/methanol mixture as the mobile phase.

Compounds I in which the radical $R^4—R^3—CONH—$ is in the para-position (I)

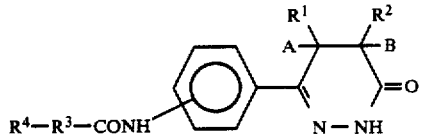

| Example No. | $R^4—R^3—[X\ H_2O]$ | | $R^1$ | $R^2$ | Mp. [°C.] | A and B | |
|---|---|---|---|---|---|---|---|
| 2 | $(H_3C)_2N—CH_2CH_2—$ | [½ $H_2O$] | $CH_3$ | H | 74–75 | H | H |
| 3 | $(H_3C)_2N—CH_2CH_2—$ | | H | H | 168–170 | H | H |
| 4 | 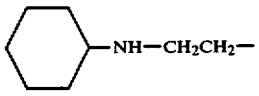 | [1 $H_2O$] | $CH_3$ | H | 143–145 | H | H |
| 5 | 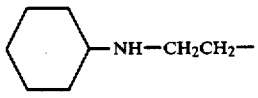 | [1,5 $H_2O$] | H | H | 168–170 | H | H |
| 6 | 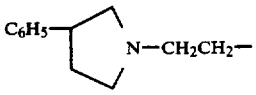 | | $CH_3$ | H | 87–89 | H | H |
| 7 | 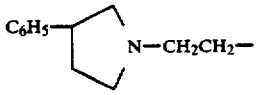 | [1 $H_2O$] | H | H | 165–166 | H | H |

-continued
Compounds I in which the radical $R^4—R^3—CONH—$ is in the para-position
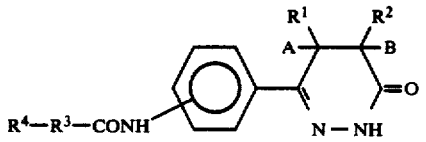
(I)
| Example No. | $R^4—R^3—[X\ H_2O]$ | | $R^1$ | $R^2$ | Mp. [°C.] | A and B | |
|---|---|---|---|---|---|---|---|
| 8 | 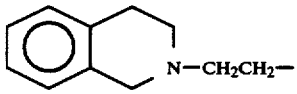 | [1 $H_2O$] | $CH_3$ | H | 119–121 | H | H |
| 9 | 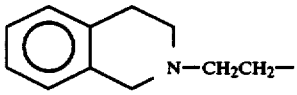 | | H | H | 191–192 | H | H |
| 10 | 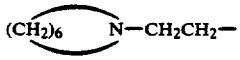 | [½ $H_2O$] | $CH_3$ | H | 180–183 | H | H |
| 11 | 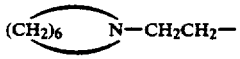 | [½ $H_2O$] | H | H | 160–162 | H | H |
| 12 | 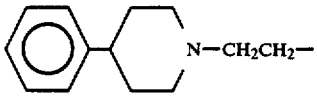 | | $CH_3$ | H | 228–230 | H | H |
| 13 | 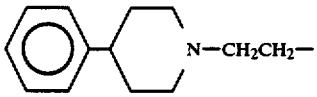 | [½ $H_2O$] | H | H | 238–240 | H | H |
| 14 | 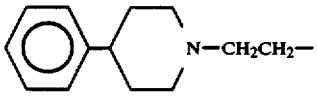 | [1 $H_2O$] | $—CH_2—$ | | 244–247 | H | H |
| 15 | 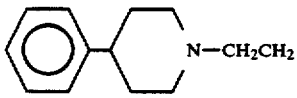 | | $—CH_2—CH_2—$ | | 240–241 | H | H |
| 16 | 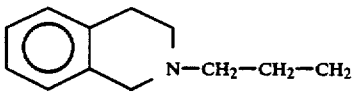 | | $CH_3$ | H | | H | H |
| 17 | 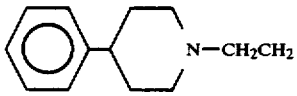 | | $—CH_2—CH_2—CH_2—CH_2—$ | | 191–192 | H | H |
| 18 | 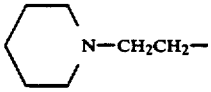 | | $CH_3$ | H | 148–150 | H | H |

-continued
Compounds I in which the radical $R^4—R^3—CONH—$ is in the para-position
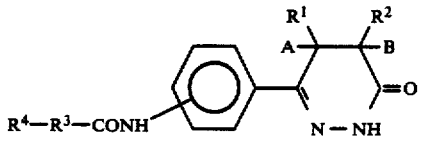
(I)
| Example No. | $R^4—R^3—[X\ H_2O]$ | | $R^1$ | $R^2$ | Mp. [°C.] | A and B | |
|---|---|---|---|---|---|---|---|
| 19 | 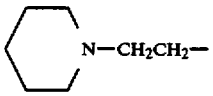 | [1 $H_2O$] | H | H | 150–152 | H | H |
| 20 | 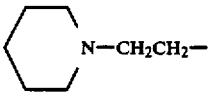 | [¼ $H_2O$] | $—CH_2—$ | | 154–155 | H | H |
| 21 | 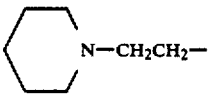 | [1.25 $H_2O$] | $—CH_2—CH_2—$ | | 115–117 | H | H |
| 22 | 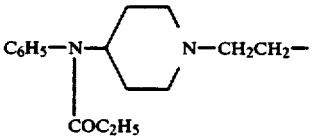 | | $CH_3$ | H | 216–217 | H | H |
| 23 | 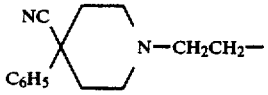 | [$H_2O$] | $CH_3$ | H | 208–210 | H | H |
| 24 | 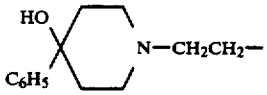 | | $CH_3$ | H | 239–240 | H | H |
| 25 | 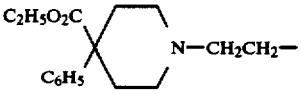 | [$H_2O$] | $CH_3$ | H | 113–115 | H | H |
| 26 | 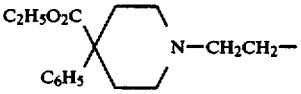 | [$H_2O$] | H | H | 197–199 | H | H |
| 27 | 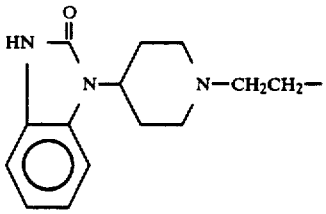 | [1 $H_2O$] | $CH_3$ | H | 168–169 | H | H |
| 28 | 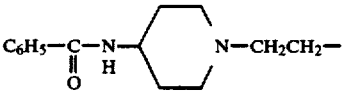 | | $CH_3$ | H | 245–247 | H | H |

-continued
Compounds I in which the radical $R^4—R^3—CONH—$ is in the para-position
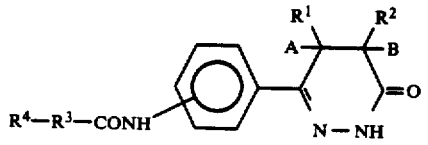
(I)
| Example No. | $R^4—R^3—[X\ H_2O]$ | | $R^1$ | $R^2$ | Mp. [°C.] | A and B | |
|---|---|---|---|---|---|---|---|
| 29 | 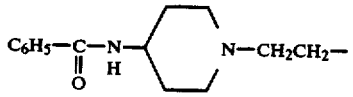 | | H | H | 261–263 | H | H |
| 30 | 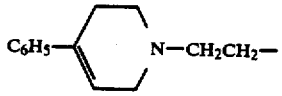 | [1 $H_2O$] | $CH_3$ | H | 204–206 | H | H |
| 31 | 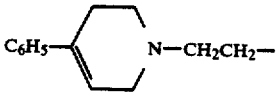 | | H | H | 235–236 | H | H |
| 32 | 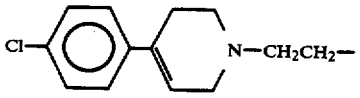 | [1 $H_2O$] | $CH_3$ | H | 200–201 | H | H |
| 33 | 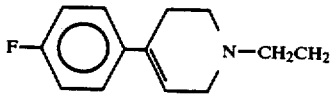 | | $CH_3$ | H | 210–212 | H | H |
| 34 | 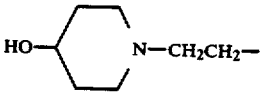 | [½ $H_2O$] | $CH_3$ | H | 187–188 | H | H |
| 35 | 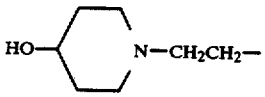 | | H | H | 216–218 | H | H |
| 36 | 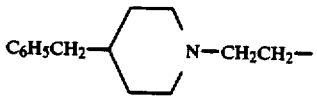 | [1 $H_2O$] | $CH_3$ | H | 190–192 | H | H |
| 37 | 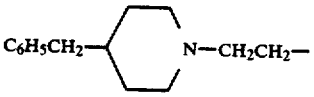 | | H | H | 192–194 | H | H |
| 38 | 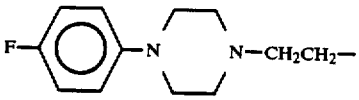 | | $[CH_2]CH_3$ | H | 223–225 | H | H |
| 39 | 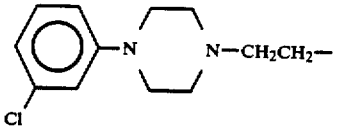 | | $CH_3$ | H | 145–147 | H | H |

-continued
Compounds I in which the radical $R^4—R^3—CONH—$ is in the para-position
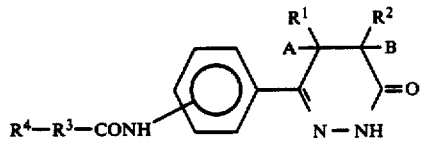
(I)
| Example No. | $R^4—R^3—[X\ H_2O]$ | | $R^1$ | $R^2$ | Mp. [°C.] | A and B | |
|---|---|---|---|---|---|---|---|
| 40 | 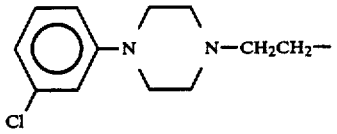 | [½ $H_2O$] | H | H | 235–236 | H | H |
| 41 | 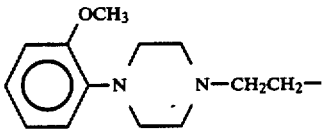 | | H | H | 207–209 | H | H |
| 42 | 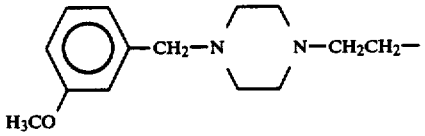 | [½ $H_2O$] | $CH_3$ | H | 86–89 | H | H |
| 43 | 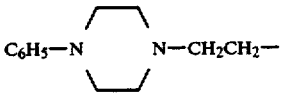 | [1.5 $H_2O$] | $CH_3$ | H | 261–263 | H | H |
| 44 | 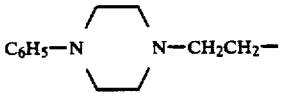 | | H | H | 255–257 | H | H |
| 45 | 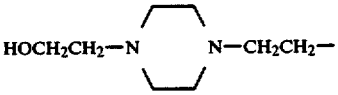 | [1 $H_2O$] | $CH_3$ | H | 228–230 | H | H |
| 46 | 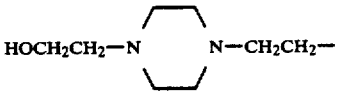 | | H | H | 219–221 | H | H |
| 47 | 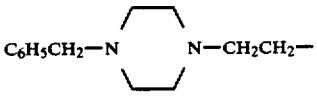 | [¼ $H_2O$] | $CH_3$ | H | 178–179 | H | H |
| 48 | 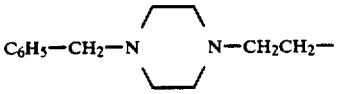 | [1 $H_2O$] | H | H | 171–173 | H | H |
| 49 | 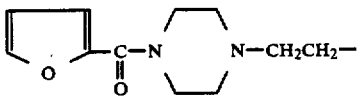 | [1 $H_2O$] | H | H | 134–136 | H | H |

-continued
Compounds I in which the radical $R^4—R^3—CONH—$ is in the para-position
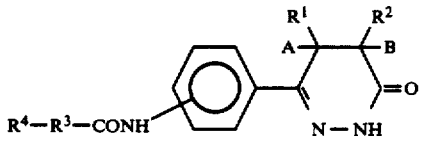
(I)
| Example No. | $R^4—R^3—[X\ H_2O]$ | | $R^1$ | $R^2$ | Mp. [°C.] | A and B | |
|---|---|---|---|---|---|---|---|
| 50 | 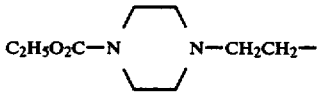 | | H | H | 200–202 | H | H |
| 51 | 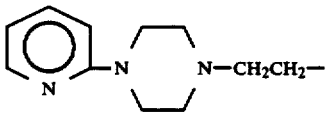 | [1.5 $H_2O$] | $CH_3$ | H | 193–195 | H | H |
| 52 | 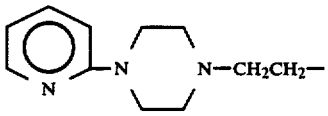 | [¼ $H_2O$] | H | H | 252–254 | H | H |
| 53 | 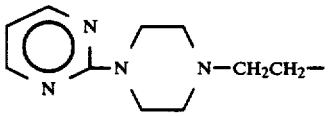 | [1 $H_2O$] | H | H | 224–225 | H | H |
| 54 | 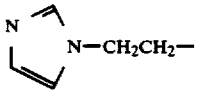 | [1 $H_2O$] | $CH_3$ | H | 198–200 | H | H |
| 55 | 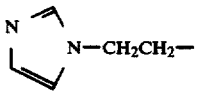 | [¼ $H_2O$] | H | H | 248–251 | H | H |
| 56 | 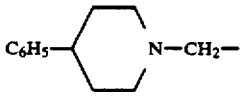 | | $CH_3$ | H | 170–171 | H | H |
| 57 | 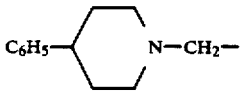 | [1 $H_2O$] | $—CH_2—$ | | 199–200 | H | H |
| 58 | 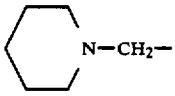 | | $—CH_2—$ | | 184–185 | H | H |
| 59 | 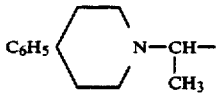 | | $CH_3$ | H | 200–202 | H | H |

-continued
Compounds I in which the radical $R^4—R^3—CONH—$ is in the para-position
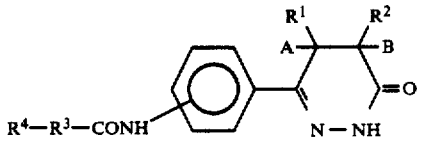
(I)
| Example No. | $R^4—R^3—[X\ H_2O]$ | | $R^1$ | $R^2$ | Mp. [°C.] | A | B |
|---|---|---|---|---|---|---|---|
| 60 | 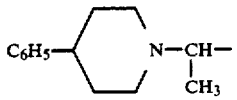 | [1 $H_2O$] | $—CH_2—$ | | 194–195 | H | H |
| 61 | 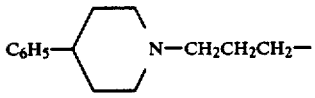 | [1 $H_2O$] | $CH_3$ | H | 112–113 | H | H |
| 62 | 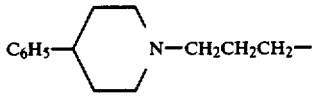 × HCl | [½ $H_2O$] | $CH_3$ | H | 295–297 | H | H |
| 63 | 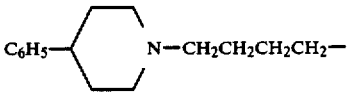 | [½ $H_2O$] | H | H | 129–130 | H | H |
| 64 | 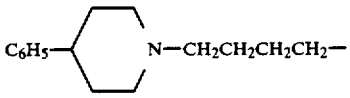 | [½ $H_2O$] | $CH_3$ | H | 115–117 | H | H |
| 65 | 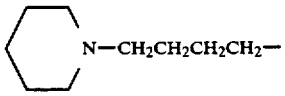 | [½ $H_2O$] | H | H | 190–192 | H | H |
| 66 | 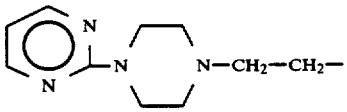 | | $CH_3$ | H | 118–124 | H | H |
| 67 | 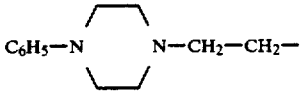 | | $—CH_2—CH_2—$ | | | H | H |
| 68 | 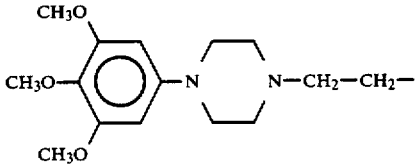 | | $CH_3$ | H | 92–96 | H | H |
| 69 | 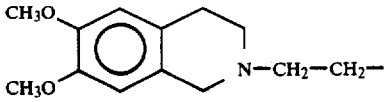 | [¾ $H_2O$] | H | H | 129–130 | H | H |

-continued
Compounds I in which the radical $R^4—R^3—CONH—$ is in the para-position
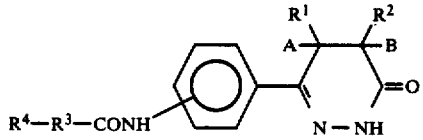
(I)
| Example No. | $R^4—R^3—[X\ H_2O]$ | $R^1$ | $R^2$ | Mp. [°C.] | A and B | |
|---|---|---|---|---|---|---|
| 70 | 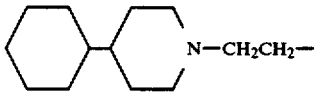 | H | H | 263-265 | H | H |
| 71 | 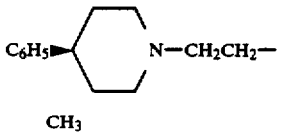 | H | H | 207-209 | H | H |
| 72 | 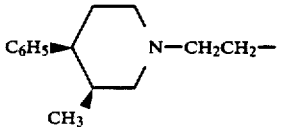 | H | H | 183-184 | H | H |
| 73 | 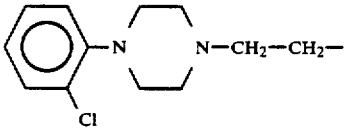 | $CH_3$ | H | 63-65 | H | H |
| 74 | 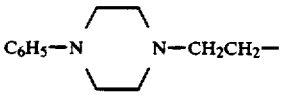 | $—CH_2—$ | | 265-267 | H | H |
| 75 | 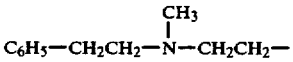 | H | H | 121-123 | H | H |
| 76 | 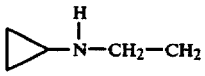 | $CH_3$ | H | | H | H |
| 77 | 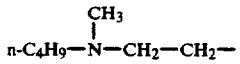 | $CH_3$ | H | 60-66 | H | H |
| 78 | 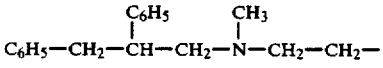 | $CH_3$ | H | | H | H |
| 79 | 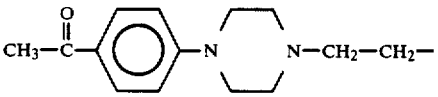 | $CH_3$ | H | 232-234 | H | H |
| 80 | 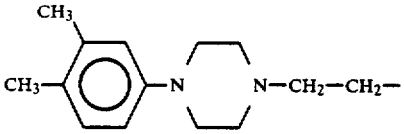 | $CH_3$ | H | 201-202 | H | H |

-continued
Compounds I in which the radical $R^4—R^3—CONH—$ is in the para-position
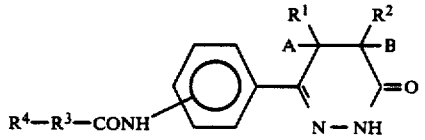
(I)
| Example No. | $R^4—R^3—[X\ H_2O]$ | $R^1$ | $R^2$ | Mp. [°C.] | A | B |
|---|---|---|---|---|---|---|
| 81 | 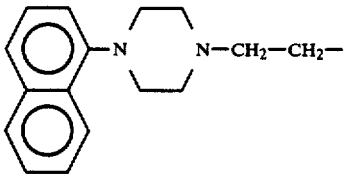 | $CH_3$ | H | | H | H |
| 82 | 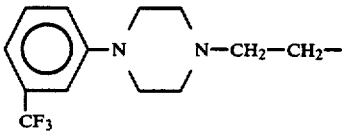 | $CH_3$ | H | 185–187 | H | H |
| 83 | 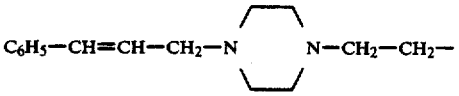 | $CH_3$ | H | oil | H | H |
| 84 | 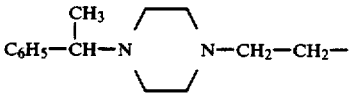 | $CH_3$ | H | 132–135 | H | H |
| 85 | 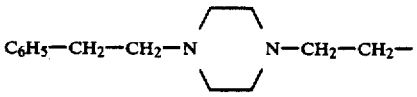 | $CH_3$ | H | 115–120 | H | H |
| 86 | 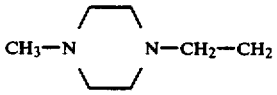 | $CH_3$ | H | oil | H | H |
| 87 | 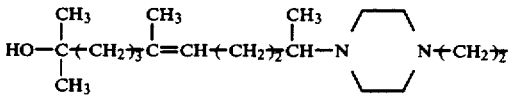 | $CH_3$ | H | oil | H | H |
| 88 | 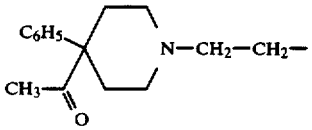 | $CH_3$ | H | 200–202 | H | H |
| 89 | 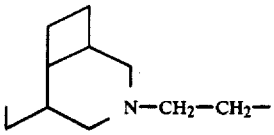 | $CH_3$ | H | 187–189 | H | H |

-continued
Compounds I in which the radical $R^4—R^3—CONH—$ is in the para-position
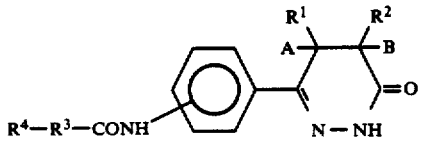
(I)
| Example No. | $R^4—R^3—[X\ H_2O]$ | $R^1$ | $R^2$ | Mp. [°C.] | A and B |
|---|---|---|---|---|---|
| 90 | 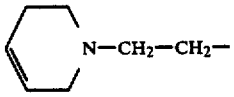 | $CH_3$ | H | 85–87 | H H |
| 91 | 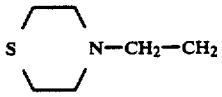 | $CH_3$ | H | 183–185 | H H |
| 92 | $n\text{-}C_4H_9—CH(C_2H_5)—CH_2—NH—CH_2—CH_2—$ | $CH_3$ | H | oil | H H |
| 93 | $n\text{-}C_{12}H_{25}—NH—CH_2—CH_2—$ | $CH_3$ | H | 123–124 | H H |
| 94 | 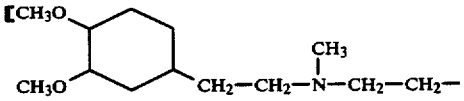 | $CH_3$ | H | 58–60 | H H |
| | 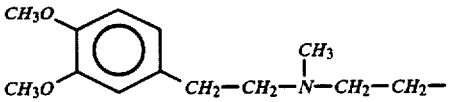 | *$CH_3$* | *H* | *58–60* | *H H* |
| 95 | $(CH_2)_7\ CH—N(CH_3)—CH_2—CH_2—$ | $CH_3$ | H | 85–87 | H H |
| 96 | 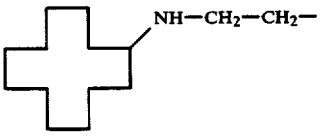 | $CH_3$ | H | 149–150 | H H |
| 97 | 1-Adamantyl-NH—$CH_2$—$CH_2$— | $CH_3$ | H | 122–126 | H H |
| 98 | 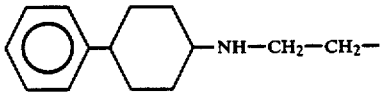 | $CH_3$ | H | 75–78 | H H |
| 99 | 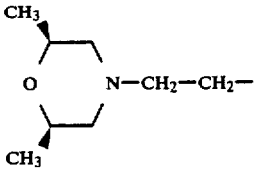 | $CH_3$ | H | 139–142 | H H |
| 100 | 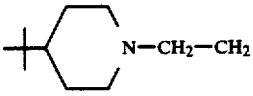 | H | H | 175–177 | H H |

-continued

Compounds I in which the radical $R^4—R^3—CONH—$ is in the para-position (I)

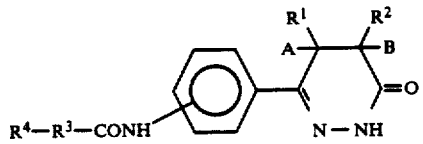

| Example No. | $R^4—R^3—[X\ H_2O]$ | $R^1$ | $R^2$ | Mp. [°C.] | A and B |
|---|---|---|---|---|---|
| 101 | 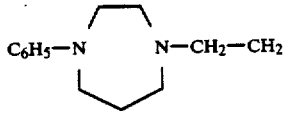 | $CH_3$ | H | | H H |
| 102 | 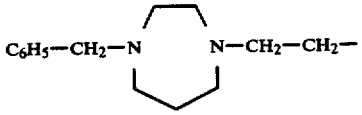 | $CH_3$ | H | | H H |
| 103 | 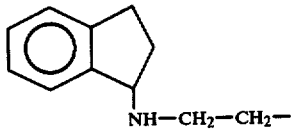 | $CH_3$ | H | | H H |
| 104 | 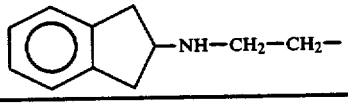 | $CH_3$ | H | 190–192 | H H |

The compounds of Examples 105 to 107 were obtained similarly to Example 1, by conversion of 6-[m-(3-chloropropionylamino)-phenyl]-4,5-dihydro-3(2H)-pyridazinone.

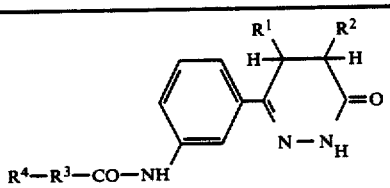

| Example No. | $R^4—R^3—[X\ H_2O]$ | $R^1$ | $R^2$ | Mp. [°C.] |
|---|---|---|---|---|
| 105 | 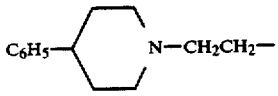 | $CH_3$ | H | 189–190 |
| 106 | 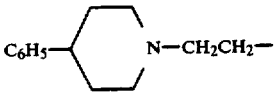 | H | H | 182–183 |
| 107 | 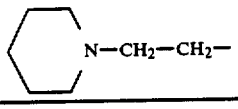 | H | H | 154–156 |

The compounds of Examples 108 to 117 were obtained from 6-[p-(3-chloropropionylamino)-phenyl]-3(2H)-pyridazinone, 6-[p-(3-chloropropionylamino)-phenyl]-5-methyl-3(2H)-pyridazinone or 6-[p-(3-chloropropionylamino)-phenyl]-4-methyl-3(2H)-pyridazinone by a method similar to that described in Example 1.

[ 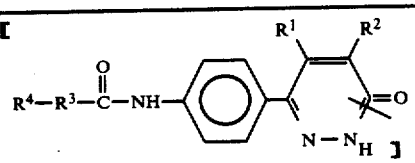 ]

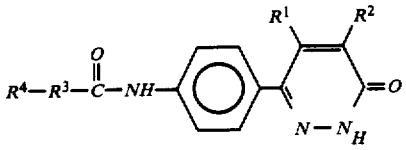

| Example No. | $R^4—R^3—[X\ H_2O]$ | $R^1$ | $R^2$ | Mp. [°C.] |
|---|---|---|---|---|
| 108 | 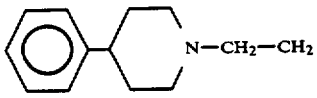 | H | H | 235–237 |

-continued

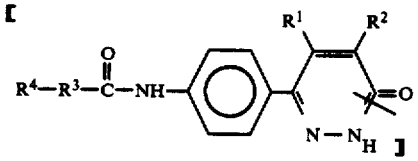

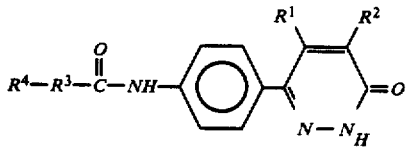

| Example No. | $R^4-R^3-[X\ H_2O]$ | $R^1$ | $R^2$ | Mp. [°C.] |
|---|---|---|---|---|
| 109 | 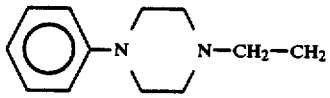 | H | H | |
| 110 | 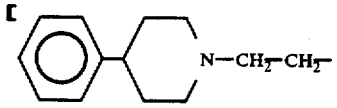 | H | H | |
| | 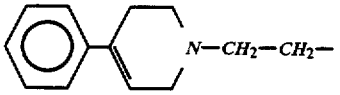 | H | H | |
| 111 | 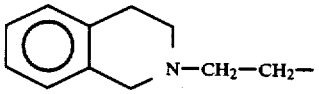 | H | H | |
| 112 | 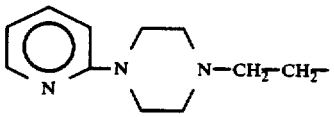 | H | H | |
| 113 | 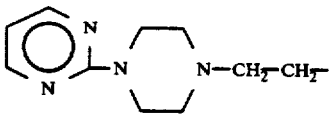 | H | H | |
| 114 | 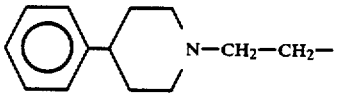 | $CH_3$ | H | |
| 115 | 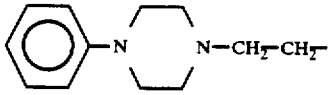 | $CH_3$ | H | |
| 116 | 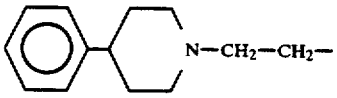 | H | $CH_3$ | 239–240 |

-continued

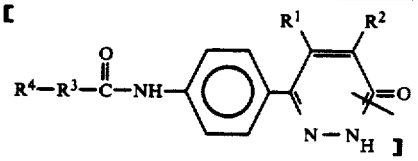

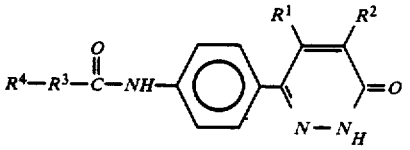

| Example No. | $R^4-R^3-[X\ H_2O]$ | $R^1$ | $R^2$ | Mp. [°C.] |
|---|---|---|---|---|
| 117 | 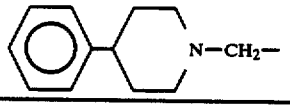 | H | H | |

EXAMPLE 118

4.0 g (10 millimoles) of 6-[p-(3-(4-phenylpiperid-1-yl)-propionylamino)-phenyl]-4,5-dihydro-3(2H)-pyridazinone in 15 ml of ethanol were refluxed with 1.5 ml of 37% strength formalin solution and 40 ml of 4% strength ethanolic KOH for 3 hours. Insoluble material was filtered off under suction, after which the mother liquor was evaporated down and the product was recrystallized from isopropanol. 2.2 g of 6-[p-(3-(4-phenylpiperid-1-yl)-propionylamino)-phenyl]-4-methyl-3(2H)-pyridazinone were obtained as pale beige crystals of melting point 239°–240° C.

EXAMPLE 119

6-[p-(3-(4-Phenylpiperazin-1-yl)-propionylamino)-phenyl]-4-methyl-3(2H)-pyridazinone was prepared from 6-[p-(3-(4-phenylpiperazin-1-yl)-propionylamino)-phenyl]-4,5-dihydro-3(2H)-pyridazinone by a method similar to that described in Example 118.

The compounds of Examples 120 to 130 were obtained by reacting a 6-[p-(chloro- or ]bromoalkanoylamino)-phenyl]-5-methyl-3(2H)-pyridazinone] *bromoalkanoylamino)-phenyl]-4,5-dihydro-5-methyl-3(2H)-pyridazinone* with 4-phenylpiperidine or phenylpiperazine by a method similar to that described in Examplb 1.

| Example | $R^4-R^3[x\ H_2O]$ | $R^1$ | $R^2$ | Mp. [°C.] |
|---|---|---|---|---|
| 120 | 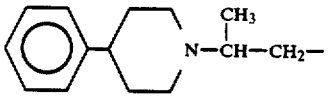 | $CH_3$ | H | |
| 121 | 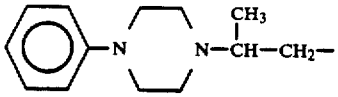 | $CH_3$ | H | |

-continued

| Example | $R^4—R^3[x\ H_2O]$ | $R^1$ | $R^2$ | Mp. [°C.] |
|---|---|---|---|---|
| 122 | 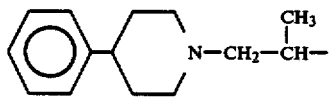 | $CH_3$ | H | |
| 123 | 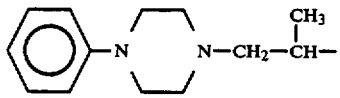 | $CH_3$ | H | |
| 124 | 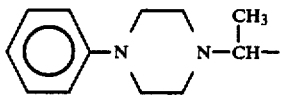 | $CH_3$ | H | |
| 125 | 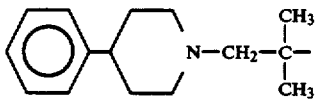 | $CH_3$ | H | |
| 126 | 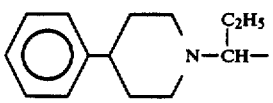 | $CH_3$ | H | |
| 127 | 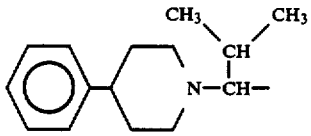 | $CH_3$ | H | |
| 128 | 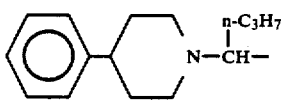 | $CH_3$ | H | |
| 129 | 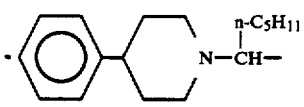 | $CH_3$ | H | |
| 130 | 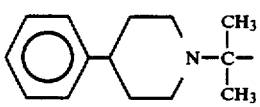 | $CH_3$ | H | |

EXAMPLE 131

6-{p-[3-(4-Phenylpiperidino)-propionylamion]-phenyl{-4,5-dihydro-3(2H)-pyridazinone A. 3-[p-(3-Chloropropionylamino)-benzoyl]-propionic acid 19.2 g (100 millimoles) of 3-(p-aminobenzoyl)-propionic acid were stirred with 24.8 g (195 millimoles) of 3-chloropropionyl chloride in 200 ml of absolute acetone for 10 hours at room temperature. The mixture was then evaporated down, the residue was stirred with 200 ml of water, and the product was filtered off under suction at 10° C., washed with cold acetone and dried at 100° C. under reduced pressure. 21 g (75%) of 3-[p-(3-chloropropionylamino)-benzoyl]-propionic acid were obtained as yellowish crystals of melting point 181°-182° C. (acetonitrile).

B.

3-{p-[3-(4-Phenylpiperidino)-propionylamino]-benzoyl}-propionic acid 56 g (200 millimoles) of 3-[p-(3-chloropropionylamino)-benzyl]-propionic acid were stirred with 60.7 g (440 millimoles) of potassium carbonate and 35.5 g (220 millimoles) of phenylpiperidine in 900 ml of dimethylformamide for 8 hours at 80° C. 2 kg of ice/water were added, after which the crystals were filtered off under suction and recrystallized from dimethylformamide/water, and the product was dried at 50° C. under greatly reduced pressure. 70 g (86%) of 3-{p-[3-(4-phenylpiperidino)propionylamino]-benzoyl}-propionic acid were obtained as colorless crystals of melting point 237°-238° C.

C.

6-{p-[3-(4-Phenylpiperidino)-propionylamino]-phenyl}-4,5-dihydro-3(2H)-pyridazinone 10 g (23.7 millimoles) of 3-{p-[3-(4-phenylpiperidino)-propionylamino]-benzoyl}-propionic acid were stirred with 1.2 g (23.7 millimoles) of hydrazine hydrate in 200 ml of ethanol for 5 hours at 80° C. The product was filtered off under suction and recrystallized from dimethylformamide/water. 7.6 g (78%) of 6-{p-[3-(4-phenylpiperidino)-propionylamino]-phenyl}-4,5-dihydro-3(2H)-pyridazinone.$\frac{1}{4}H_2O$ were obtained as colorless crystals of melting point 238°-240° C.

The compounds of Examples 1 to 130 can be prepared similarly to Example 131.

EXAMPLE 132

6-{p-[3-(2-Phenylethylamino)-propionylamino]-phenyl}-4,5-dihydro-3(2H)-pyridazinone 11.18 g (40 millimoles) of 6-[p-(3-chloropropionylamino)-phenyl]-4,5-dihydro-3(2H)-pyridazinone in 250 ml of ethanol were initially taken and 26.5 g (220 millimoles) of 2-phenylethylamine were added dropwise, after which the mixture was refluxed for 6 hours. Insoluble material was filtered off, the solvent was stripped off and the mother liquor was then crystallized by adding acetone. The product was recrystallized twice from methanol to give 5.3 g of 6-{p-[3-(2-phenylethylamino)-propionylamino]-phenyl}-4,5-dihydro-3(2H)-pyridazinone.HCl of melting point 269°-270° C.

For conversion to the free base, the hydrochloride obtained as described above was dissolved in methanol, and an equimolar amount of sodium methylate was added. The solvent was stripped off and $H_2O$ was added, after which the substance was extracted with methylene chloride, the methylene chloride phase was dried over $Na_2SO_4$, the solvent was stripped off and the substance was stirred with acetone and then filtered off under suction. 6-{p-[3-(2-phenylethylamino)-propionylamino]-phenyl}-4,5-dihydro-3(2H)-pyridazinone of melting point 130°-132° C. was obtained.

Pharmaceutical examples (A) Preparation of tablets

| Composition | |
|---|---|
| Active compound | 10 mg |
| Polyvinylpyrrolidone (mean molecular weight 25,000) | 170 mg |
| Polyethylene glycol (mean molecular weight 4,000) | 14 mg |
| Hydroxypropylmethylcellulose | 40 mg |
| Talc | 4 mg |

-continued

| Pharmaceutical examples (A) Preparation of tablets | |
|---|---|
| Composition | |
| Magnesium stearate | 2 mg |
| | 240 mg |

The active compound is moistened with a 10% strength aqueous solution of polyvinylpyrrolidone and forced through a sieve of 1.0 mm mesh size, and the granules are dried at 50° C. They are then mixed with polyethylene glycol (mean molecular weight 4,000), hydroxypropylmethylcellulose, talc and magnesium stearate, and the mixture is pressed to give tablets weighing 280 mg.

| (B) Preparation of coated tablets | |
|---|---|
| Composition of the tablet cores | |
| Active compound | 10 mg |
| Lactose | 90 mg |
| Corn starch | 60 mg |
| Polyvinylpyrrolidone | 6 mg |
| Magnesium stearate | 1 mg |
| | 167 mg |

The active compound, lactose and corn starch are mixed, moistened with an 8% strength aqueous solution of the polyvinylpyrrolidone, and granulated by passing through a sieve of 1.5 mm mesh size. The granules are dried at 50° C. and forced through a 1.0 mm sieve. The granules thus obtained are mixed with magnesium stearate, and the mixture is pressed to form tablet cores. These are coated in a conventional manner with a shell consisting essentially of sugar and talc.

We claim:

1. A 6-(alkanoylaminoaryl)-3(2H)-pyridazinone derivative of the formula I

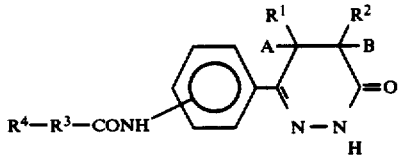

(I)

wherein the substituents on the phenylene radical are para to one another, A and B are each hydrogen or together form a bond, $R^1$ is hydrogen or methyl, $R^2$ is hydrogen or, where A and B are each hydrogen $R^1$ and $R^2$ together form a $C_1$–$C_2$-alkylene radical, $R^3$ is a straight-chain [$C_1$–$C_4$-alkylene] *$C_2$–$C_4$-alkylene* group which can be substituted by $C_1$–$C_3$-alkyl group or by two methyl groups, and $R^4$ is (b) a group of the formula II

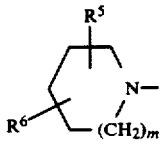

(II)

where the broken line can be an additional bond, $R^5$ is $C_1$–$C_4$-alkyl which is [unsubstituted or] substituted by phenyl, or phenyl which is unsubstituted or substituted by 1 or 2 halogen atoms, or is a group of the formula $R^7R^8N$, where $R^7$ is hydrogen or phenyl, and $R^8$ is $C_1$–$C_4$-acyl or benzoyl, or $R^7$ and $R^8$, together with the nitrogen atom, form a benzimidazol-2-on-1-yl group, $R^6$ is $C_1$–$C_4$-alkyl, hydroxyl, $C_1$–$C_4$-acyl, ($C_1$–$C_5$-alkoxy)-carbonyl or cyano, or $R^5$ and $R^6$ together form a $C_1$–$C_4$-alkylene chain, and m is 0, 1 or 2, or (c) a group of the formula III

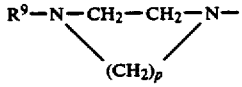

['] where $R^9$ is a $C_1$–$C_3$-hydrocarbon radical [which may be] substituted by phenyl or a $C_3$–$C_8$-cycloalkyl (in which case a $C_5$–$C_8$-cycloalkyl group can be benzofused) or $C_6$–$C_{10}$-aryl which can contain 1 to 3 $C_1$–$C_4$-alkyl, $C_1$–$C_4$-alkoxy, trifluoromethyl, nitro, hydroxyl, $C_1$–$C_4$-acyl, carboxyl, ($C_1$–$C_5$-alkoxy)-carbonyl, amido, N-($C_1$–$C_4$-alkyl)amido, N,N-di-($C_1$–$C_4$-alkyl)amido, tri($C_1$–$C_4$-alkyl)-silyl, cyano, amino, $C_1$–$C_4$-alkylamino, di-($C_1$–$C_4$-alkyl)amino, $C_1$–$C_4$-alkanoyl amino groups and/or halogen atoms; a $C_6$–$C_{10}$-aroyl group which is unsubstituted or substituted by 1 to 3 $C_1$–$C_4$-alkyl, $C_1$–$C_4$-alkoxy, trifluoromethyl, nitro, hydroxyl, $C_1$–$C_4$-alkanoyl, carboxyl, $C_1$–$C_5$-alkoxy-carbonyl, N,N-di-($C_1$–$C_4$-alkyl)-amido, cyano, di-($C_1$–$C_4$-alkyl)-amino groups and/or halogen atoms; or a hetaroyl group having 5 to 6 ring members, which can contain 1 to 3 hetero atoms and may be benzofused; a $C_3$–$C_{12}$-cycloalkyl, $C_1$–$C_8$-acyl or ($C_1$–$C_5$-alkoxy)-carbonyl group or a $C_6$–$C_{10}$-aryl radical which is unsubstituted or monosubstituted, disubstituted or trisubstituted by halogen, $C_1$–$C_4$-alkyl, $C_1$–$C_4$-alkoxy, hydroxyl, trifluoromethyl, $C_1$–$C_4$-acyl, carboxyl, ($C_1$–$C_5$-alkoxy)-carbonyl, cyano, nitro, amino, $C_1$–$C_4$-alkylamino, di-$C_1$–$C_4$-alkylamino, arylamino or $C_1$–$C_4$-acylamino; or a 5-membered or 6-membered hetaryl radical which may be benzofused, contains 1 to 3 nitrogen atoms and may or may not contain an oxygen atom or sulfur atom, and p is 2 or 3, or (e) a group of the formula V

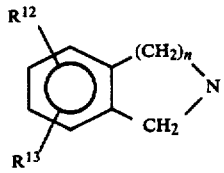

(V)

where $R^{12}$ and $R^{13}$ are each hydrogen, halogen, $C_1$–$C_4$-alkyl or $C_1$–$C_4$-alkoxy, and n is 1, 2 or 3.

2. 6-{p-[3-(4-Phenyl-1-piperazino)-propionylamino]-phenyl}-5-methyl-4,5-dihydro-3(2H)-pyridazinone.

3. 6-{p-[3-(4-Phyrid-2-yl-1-piperazino)-propionylamino]-phenyl}-5-methyl-4,5-dihydro-3(2H)-pyridazinone.

4. 6-{p-[3-(4-Benzyl-1-piperazino)propionylamino]-phenyl}-5-methyl-4,5-dihydro-3(2H)-pyridazinone.

5. 6-{p-[2-(5-Phenyl-1-piperidino)-acetylamino]-phenyl}-5-methyl-4,5-dihydro-3(2H)-pyridazinone.

6. 6-{p-[3-(4-Phenyl-1-piperidino)-propionylamino]-phenyl}-4,5-dihydropyridazinone.

7. 6-{p-[3-(4-Phenyl-1-piperidino)-propionylamino]-phenyl}-5-methyl-4,5-dihydropyridazinone.

8. [2-{p-[3-(4-Phenyl-1-piperidino)-propynylamino]-phenyl}-3,4-diazabicyclo[4.1.0]hept-2-en-5-one] *2-{p-*

*[3-(4-Phenyl-1-piperidino)-propionylamino]-phenyl}-3,4-diazabicyclo[4.1.0]hept-2-en-5-one.*

9. 6-{p-[3-(4-Phenyl-1-(1,2,3,6-tetrahydropyridino)-propionylamino]-phenyl}-5-methyl-4,5-dihydro-3(2H)-pyridazinone.

10. 6-{p-[3-(4-Phenyl-1-piperidino)-propionylamino]-phenyl}-3(2H)-pyridazinone.

11. 6-{p-[3-(1,2,3,4-Tetrahydroisoquinolino)propionylamino]-phenyl}-5-methyl-4,5-dihydro-3(2H)-pyridazinone.

12. A [therapeutic] *pharmaceutical* composition *having thrombocyte aggregation-inhibiting activity* comprising [a pharmaceutical expedient and] an effective amount of a 6-(alkanoyl-aminoaryl)-3(2H)-pyridazinone derivative as claimed in claim [16] *1* as the active compound.

13. The method of treating disease caused by thrombocyte aggregation in a patient suffering therefrom which comprises administering an effective amount of a 6-(alkanoyl-aminoaryl)-3(2H)-pyridazinone derivative as claimed in claim [12] *1*.

* * * * *

UNITED STATES PATENT AND TRADEMARK OFFICE

CERTIFICATE OF CORRECTION

PATENT NO. : Re 33,476

DATED : December 4, 1990

INVENTOR(S) : Phillip ROSSY et al.

It is certified that error appears in the above-identified patent and that said Letters Patent is hereby corrected as shown below:

Claim 1, Line 13:

formula II " 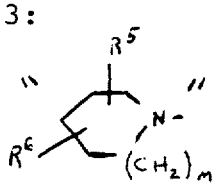 " should read -- 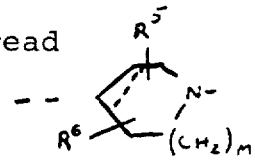 --

Claim 3, Line 1: "Phyrid" should read --Pyrid--

Claim 5, Line 1: "5" should read --4--

Claim 11, Line 1: insert --(1- -- between "3-" and "(1"

Signed and Sealed this

Fourteenth Day of May, 1991

*Attest:*

*Attesting Officer*

HARRY F. MANBECK, JR.

*Commissioner of Patents and Trademarks*